United States Patent
Feng

(10) Patent No.: US 9,573,976 B2
(45) Date of Patent: *Feb. 21, 2017

(54) ANTAGONIST FOR (PRO)RENIN RECEPTOR FOR THE TREATMENT OF HYPERTENSION AND DIABETES

(71) Applicant: University of Utah, Salt Lake City, UT (US)

(72) Inventor: Yumei Feng, Fort Collins, CO (US)

(73) Assignee: UNIVERSITY OF UTAH RESEARCH FOUNDATION, Salt Lake City, UT (US)

(*) Notice: Subject to any disclaimer, the term of this patent is extended or adjusted under 35 U.S.C. 154(b) by 0 days.

This patent is subject to a terminal disclaimer.

(21) Appl. No.: 14/429,733

(22) PCT Filed: Sep. 18, 2013

(86) PCT No.: PCT/US2013/060437
§ 371 (c)(1),
(2) Date: Mar. 19, 2015

(87) PCT Pub. No.: WO2014/047194
PCT Pub. Date: Mar. 27, 2014

(65) Prior Publication Data
US 2015/0252074 A1    Sep. 10, 2015

Related U.S. Application Data

(60) Provisional application No. 61/703,205, filed on Sep. 19, 2012.

(51) Int. Cl.
| | | |
|---|---|---|
| *C07K 7/08* | (2006.01) | |
| *C07K 7/06* | (2006.01) | |
| *C07K 14/00* | (2006.01) | |
| *C07K 14/47* | (2006.01) | |
| *C07K 14/705* | (2006.01) | |
| *A61K 38/00* | (2006.01) | |
| *A61K 9/00* | (2006.01) | |

(52) U.S. Cl.
CPC .......... *C07K 7/08* (2013.01); *C07K 14/00* (2013.01); *C07K 14/4703* (2013.01); *C07K 14/4705* (2013.01); *C07K 14/705* (2013.01); *A61K 9/0019* (2013.01); *A61K 9/0085* (2013.01); *A61K 38/00* (2013.01)

(58) Field of Classification Search
CPC ............ C07K 7/08; C07K 14/00; C07K 7/06; C07K 14/001
See application file for complete search history.

(56) References Cited

U.S. PATENT DOCUMENTS

| | | |
|---|---|---|
| 5,579,250 A | 11/1996 | Balaji et al. |
| 5,612,895 A | 3/1997 | Balaji et al. |
| 5,631,280 A | 5/1997 | Ciccarone et al. |
| 2003/0165999 A1* | 9/2003 | Ishida ............... C07K 14/4705 435/7.1 |
| 2005/0037007 A1 | 2/2005 | Noble et al. |
| 2005/0203021 A1 | 9/2005 | Ishida et al. |
| 2008/0161321 A1 | 7/2008 | Feldman et al. |
| 2011/0091427 A1 | 4/2011 | Amrani et al. |
| 2014/0094409 A1 | 4/2014 | Feng |

FOREIGN PATENT DOCUMENTS

WO    WO-2014/047194 A1    3/2014

OTHER PUBLICATIONS

G.N. Moll, A biological stabilization technology for peptide drugs: enzymatic introduction of thioether-bridges, Drug Discovery Today: Technologies, vol. 6, No. 1-4, 2009.*
DeMello, et al., Renin Angiotensin System and Cardiovascular Disease, 2009, Chapter 3, Renin, Prorenin and Pro Renin Receptor, pp. 15-24. Genevieve Nguyen and Aurelie Contrepas.
Garg, et al., "Review article: the pathophysiological roles of the renin-angiotensin system in the gastrointestinal tract", (2012) vol. 35(4) (pp. 414-428).
Jiqan Huang, Renal (pro)renin receptor contributes to development of diabetic kidney disease through TGFβ1-CTGF signaling cascade, Clin Exp Pharmacal Physiol. Apr. 2011; 38(4): 215-221.
International Search Report and Written Opinion mailed on Oct. 16, 2015 by the International Searching Authority for International Patent Application No. PCT/US2015/43085, filed on Jul. 31, 2015 (Inventor-Feng // Applicant-Univ. of Utah Research Foundation) (31 pages).
Non-Final Office Action issued on Dec. 1, 2015 by the U.S. Patent & Trademark Office for U.S. Appl. No. 14/499,714, filed Aug. 1, 2014 and published as US 2015/0025013 on Jan. 22, 2015 (Inventor-Feng // Applicant-Univ. Utah Research Foundation) (17 pages).
Achard, V. et al., Renin Receptor Expression in Human Adipose Tissue, Am J Physiol Regul Integr Comp Physiol, 292:R274-282 (2007).
Allen, A.M., Inhibition of the Hypthalamic Paraventricular Nucleus in Spontaneously Hypertensive Rats Dramatically Reduces Sympathetic Vasomotor Tone, Hypertension, 39:275-280 (2002).
Ausubel et al., Current Protocols in Molecular Biology, John Wiley & Sons, Inc., New York (1999).
Bader M. et al., It's Renin in the Brain: Transgenic Animals Elucidate the Brain Renin-Angiotensin System, Circ Res., 90:8-10 (2002).

(Continued)

*Primary Examiner* — James H Alstrum Acevedo
*Assistant Examiner* — Erinne Dabkowski
(74) *Attorney, Agent, or Firm* — Ballard Spahr LLP

(57) ABSTRACT

Methods and compositions for increasing a plant's resistance to an insect pest such as the corn rootworm are provided. Methods are provided for overexpression of Crw2, or variants thereof, in a host plant or plant cell to increase resistance to an insect pest in a plant such as maize. Methods are also provided for identifying variants of Crw2 that when incorporated into a plant via transgenic or traditional breeding means increase resistance to an insect pest in a plant such as maize. Also provided are methods for increasing resistance by overexpressing Crw1 and Crw2.

7 Claims, 21 Drawing Sheets

(56) References Cited

OTHER PUBLICATIONS

Batenburg, W.W. et al., Prorenin is the endogenous agonist of the (pro)renin receptor. Binding kinetics of renin and prorenin in rat vascular smooth muscle cells overexpressing the human (pro)renin receptor, J Hypertens 25(12):2441-2453 (2007).
Berecek K.H. et al., Vasopressin and Vascular Reactivity in the Development of DOCA Hypertension in Rats with Heredity Diabetes Insipidus, Hypertension, 4(1):3-12 (1982).
Bierbaum, G. et al., Engineering of a Novel Thiother Bridge and Role of Modified Residues in the Lantibiotic PepS, Applied and Environmental Microbiology, 62(2):385-392 (1996).
Biswas, K.B. et al., Species Specificity of Prorenin binding to the (pro)renin receptor in vitro, Front Biosci E2, 2:1234-1240 (2010).
Blaustein, M.P. et al., How NaCl Raises Blood Pressure: a New Paradigm for the Pathogenesis of Salt-Dependent Hypertension, Am J Physiol Heart and Circ Physiol, 302:H1031-H1049 (2012).
Brewer, G.J. et al., Isolation and Culture of Adult Neurons and Neurospheres, Nat. Protocols, 2(6):1490-1498 (2007).
Bubien, J. K., Epithelial Na+ channel (ENaC), Hormones, and Hypertension, J Bioi Chern 285(31):23527-23531 (2010).
Burckle, C. et al., Prorenin and Its Ancient Receptor. Hypertension 48:549-551 (2006).
Chen, Q.H. et al., $AT_1$-Receptor Blockade in the Hypothalamic PVN Reduces Central Hyperosmolality-Induced Renal Sympathoexcitation, Am J Physiol Regulatory Integrative Comp Physiol, 281:R1844-R1853 (2001).
Chen, X. et al., Targeting Deletion of Angiotensin Type 1B Receptor Gene in the Mouse, Am J Physiol, 272:F299-F304 (1997).
Chou, C.L. et al., Regulation of Aquaporin-2 Trafficking by Vasopressin in the Renal Collecting Duct: Roles of Ryanodine-Sensitive $Ca^{2+}$ Stores and Calmodulin, J Bioi Chem, 275(47):36839-36846 (2000).
Cold Spring Harbor Laboratories; Goding (1986) Monoclonal Antibodies: Principles and Practice, 2d ed., Academic Press, New York.
Connelly, K.A. et al., The Cardiac (Pro)Renin Receptor is Primarily Expressed in Myocyte Transverse Tubules and it Increased in Experimental Diabetic Cardiomyopathy, Journal of Hypertension, 29(6): 1175-1184 (2011).
Cousin, C. et al., Soluble Form of the (Pro )Renin Receptor Generated by Intracellular Cleavage by Furin is Secreted in Plasma, Hypertension 53:1077-1082 (2009).
Creighton, T.E., Proteins- Structure and Molecular Properties 2nd Ed., W.H. Freeman and Company, New York (1993).
Crider, B.P. et al., Characterization of the functional Coupling of Bovine Brain Vacular-type H+- translocating ATPase, J Bioi Chem, 278(45):44281-44288 (2003).
Crowley, S.D. et al., Angiotensin II causes hypertension and cardiac hypertrophy through its receptors in the kidney, Proc Natl A cad Sci U.S.A., 103(47):17985-17990 (2006).
Cruciat, C.M. et al., Requirement of Preorenin Receptor and Vacular H+-ATPase: Mediated Acidification for Wnt Signaling, Science, 327(22):459-463 (2010).
Cuadra, A.E. et al., A Current View of Brain Renin-Angiotensin System: Is the (Pro)renin Receptor the Missing Link?, Pharmacol Ther., 2010, 125(1):27-38 (2010).
Dahlöf, B. et al., Cardiovascular morbidity and mortality in the Losartan Intervention for Endpoint reduction in hypertension study (LIFE): A randomised trial against atenolol, The Lancet 359:995-1003 (2002).
Danser, A.H.J. et al., Renin, Prorenin and the Putative (Pro)renin Receptor, Hypertension, 46:1069-1076 (2005).
Danser, A.H.J., The Increase in Renin During Renin Inhibition: Does it result in Harmful Effects by the (Pro)renin Receptor?, Hypertens Res., 33:4-10 (2009).
Danser, A.H.J. et al., Prorenin and the (pro)renin receptor—an update, Nephrol Dial Transplant, 22:1288-1292 (2007).
Davisson, R.L., et al., Transgenic Animal Models as Tools for Studying Renal Developmental Phsiology, Pediatr Nephrol., 10:798-803 (1996).
Davisson, R.L., Physiological Genomic Analysis of the Brain Renin-Angiotensin System, Am J Physiol Regul Integr Camp Physiol, 285:R498-R511 (2003).
de Vries, L. et al., Oral and Pulmonary Delivery of Thioether-Bridged Angiotensin-(1-7), Peptides 31, 893-898 (2010).
Eide, L. et al., Culture of Adult Mouse Neurons, Biotechniques, 38:99-104 (2005).
Facemire, C.S. et al., The Impact of Microsomal Prostaglandin E Synthase 1 on Blood Pressure is Determined by Genetic Background, Hypertension 55(part 2):531-538 (2010).
Feldt, S. et al., Prorenin and Renin-Induced Extracellular Signal-Regulated Kinase ½ Activation in Monocytes is Not Blocked by Aliskiren or the Handle-Region Peptide, Hypertension, 51 :682-688 (2008).
Feldt, S. et al., The Putative (Pro )renin Receptor Blocker HRP Fails to Prevent (Pro )renin Signaling, J Am Soc Nephrol, 19:743-748 (2008).
Feng, Y. et al., Angiotensin-Converting Enzyme 2 Overexpression in the Subfornical Organ Prevents the Angiotensin II-Mediated Pressor and Drinking Responses and is Associated with Angiotensin II Type 1 Receptor Downregulation, Circ Res, 102:729-736 (2008).
Feng, Y. et al., Brain-Selective Overexpression of Human Angiotensin-Converting Enzyme Type 2 Attenuates Neurogenic Hypertension, Circ Res, 106:373-382 (2010).
Feng, Y. et al., $ACE_2$ Prevention of Oxidative Stress in the Brain is Associated with a Reduction in Angiotensin II-Induced Sympathetic Vasomodulation, FASEB J, 23:802.801 (2009).
Ferrario, C.M., ACE2: more of Ang-(1-7) or less Ang 11?, Curr Opin Nephrol Hypertens, 20:1-6 (2011).
Ferrario, C.M., Angiotensin-Converting Enzyme 2 and Angiotensin-(1-7): An Evolving Story in Cardiovascular Regulation, Hypertension, 47(part 2):515-521 (2006).
Ferreira, A.J. et al., Evidence for Angiotensin-Converting Enzyme 2 as a Therapeutic Target for the Prevention of Pulmonary Hypertension, Am J Respir Crit Care Med, 179:1048-1054 (2009).
Fisher, J.P. et al., Therapeutic Strategies for Targeting Excessive Central Sympathetic Activation in Human Hypertension, Exp Physiol, 95:572-580 (2010).
Freeman, K.L. et al., $AT_1$ and Glutamatergic Receptors in Paraventricular Nucleus Support Blood Pressure During Water Deprivation, Am J Physiol Regul Integr Comp Physiol, 292:R1675-1682 (2007).
Galvez, O.G. et al., Studies of the Mechanism of Contralateral Polyuria after Renal Artery Stenosis, J Clin Invest, 59:609-615 (1977).
Garty, H. et a., Epithelial Sodium Channels: Function, Structure, and Regulation, Physiol Rev 77(2):359-396 (1997).
Gennaro, A.R., Remington: The Science and Practice of Pharmacy (19th ed.), Mack Publishing Company, Easton, PA (1995).
Giese, M.J. et al., 2013. The ocular renin-angiotensin system: A therapeutic target for the treatment of ocular disease, Pharmacol Ther 142:11-32 (2014).
Gonzalez, A.A. et al., Soluble Form of the (Pro)Renin Receptor is Augmented in the Collecting Duct and Urine of Chronic Angiotensin II-Dependent Hypertensive Rats, Hypertension, 57:859-864 (2011).
Gonzalez, A.A. et al., Angiotensin II Stimulates Renin in Inner Medullary Collecting Duct Cells via Protein Kinase C and Independent of Epithelial Sodium Channel and Mineralocorticoid Receptor Activity, Hypertension, 57(part 2):594-599 (2011).
Grobe, J.L. et al., Angiotensinergic Signaling in the Brain Mediates metabolic Effects of Deoxycoticosterone (DOCA)-Salt in C57 Mice, Hypertension, 57(part 2):600-607 (2011).
Gutkind, J.S. et al., Increased Angiotensin II Receptors in Brain Nuclei of DOCA-Salt Hypertensive Rats, Am J Physiol, 255:H646-H650 (1988).
Hamada, K. et al., Serum Level of Soluble (Pro )renin Receptor is Modulated in Chronic Kidney Disease, Clin Exp Nephrol, 17:848-856 (2013).
Hans, C.P. et al., Opposing Roles of PARP-1 in MMP-9 and TIMP-2 Expression and Mast Cell Degranulation in Dyslipidemic Dilated Cardiomyopathy, Cardiovasc Pathol, 20:e57-e68 (2010).

(56) References Cited

OTHER PUBLICATIONS

Hans, C.P., et al., Protective Effects of PARP-1 Knockout on Dysliidemia-Induced Autonomic and Vascular Dysfunction in ApoE−/− Mice: Effects on eNOS and Oxidative Stress, PLoS One, 4(10):e7430, pp. 1-11 (2009).
Hansson, L. et al., 1999. Effect of angiotensin-converting-enzyme inhibition compared with conventional therapy on cardiovascular morbidity and mortality in hypertension: the Captopril Prevention Project (CAPPP) randomised trial, The Lancet 353:611-616 (1999).
Harlow and Lane (1988) Antibodies: A Laboratory Manual.
Hirose T. et al., Association of (Pro)renin Receptor Gene Polymorphism with Blood Pressure in Japanese Men: The Ohasama Study, Am J Hypertens, 22(3):294-299 (2009).
Hou X, et al., Enhanced Pressor Response in Increased CSF Sodium Concentration and to Central ANG I Heterozygous $\alpha_2$ Na+-K+-ATPase Knockout Mice, Am J Physiol Regul Integr Comp Physiol, 296:R1427-R1438 (2009).
Huang, B.S. et al., Increases in CSF [Na+] Precede the Increases in Blood Pressure in Dahl A Rats and SHR on a High-Salt Diet, Am J Physiol Heart Circ Physiol, 287:H1160-H1166 (2004).
Ichihara, A. et al., Inhibition of Diabetic Nephropathy by a Decoy Peptide Corresponding to the "Handle" Region for Nonproteolytic Activation of Prorenin, J. Clin. Invest., 114(8):1128-1135 (2004).
Ilatovskaya, D.V. et al., ROS production as a common mechanism of ENaC regulation by EGF, insulin, and IGF-1, Am J Physiol Cell Physiol 304:C102-111 (2013).
Ito, K. et al., Acquisition of Brain Na Sensitivity Contributes to Salt-Induced Sympathoexcitation and Cardiac Dysfunction in Mice with Pressure Overload, Circ Res, 104:1004-1011 (2009).
Janiak, P.C. et al., Role of Central Mineralocorticoid Binding Sites in Development of Hypertension, Am J Physiol Regul Integr Comp Physiol, 259:R1025-R1034 (1990).
Johnson, B.C., Posttranslational Covalent Modification of Proteins, Academic Press, New York, pp. 1-12 (1983).
Kaneshiro, Y. et al., Slowly Progressive, Angiotensin II-Independent Glomerulosclerosis in Human (Pro)renin Receptor-transgenic Rats, J Am Soc Nephrol, 18:1789-1795 (200&).
Kang, J.J. et al., The Collecting Duct is the Major Source of Prorenin in Diabetes, Hypertension 51:1597-1604 (2008).
Kinouchi, K. et al., The (Pro)renin Receptor/ATP6AP2 is Essential for Vacuolar H+-ATPase Assembly in Murine Cardiomyocytes, Circ Res, 107:30-34 (2010).
Krebs, C. et al., Antihypertensive Therapy Upregulates Renin and (Pro)renin Receptor in the Clipped Kidney of Goldblatt Hypertensive Rats, Kidney Int, 72:725-730 (2007).
Krop, M. et al., The (pro)renin receptor. A decade of research: what have we learned? Pflugers Arch- EurJ Physiol 465:87-97 (2013).
Kuipers, A. et al., Translocation of a Thioether-Bridged Azurin Peptide Fragment via the Sec Pathway in *Lactococcus lactis*, Appl. Environ. Microbiol. 75(11):3800-3802 (2009).
Lal, A. et al., Prevention of High Salt Diet-Induced Cardiac Hypertrophy and Fibrosis by Spironolactone, Am J Hypertens, 16:319-323 (2003).
Lazartigues, E. et al., Brain-Selective Overexpression of Angiotensin ($AT_1$) Receptors Causes Enhanced Cardiovascular Sensitivity in Transgenic Mice, Circ Res, 90:617-624 (2002).
Lazartigues, E. et al., Endogenous Central Cholinergic Systems and Baroreflex Modulation in the Conscious Dog, Fundam Clin Pharmacol, 12:643-645 (1998).
Li, W. et al., Brain-Targeted (Pro)renin Receptor Knockdown Attenuates Angiotensin II-Dependent Hypertension, Hypertension, 59:1188-1194 (2012).
Lippoldt, A. et al., A View of Renin in the Brain, J Mol Med, 2001, 79:71-73 (2001).
Lonn, E.M. et al., Emerging role of angiotensin-converting enzyme inhibitors in cardiac and vascular protection, Circulation 90(4):2056-2069 (1994).
Ludwig, J. et al., Identification and Characterization of a Novel 9.2-kDa Membrane Sector-associated Protein of Vacuolar Proton-ATPase from Chromaffin Granules, J Biol Chem 273(18):10939-10947 (1998).
Mahmud, H. et al., Regulation of the (pro)renin-renin receptor in cardiac remodeling, J Cell Mol Med 16(4):722-729 (2012).
Makrides, S.C. et al., Regulation of Renin Gene Expression in Hypertensive Rats, Hypertension, 12:405-410 (1988).
Mamenko, M. et al., Angiotensin II Increases Activity of the Epithelial Na+ Channel (ENaC) in Distal Nephron Additively to Aldosterone, J Biol Chem, 287(1):660-671 (2012).
Merrill, D.C. et al., Chronic Hypertension and Altered Baroreflex Responses in Transgenic Mice Containing the Human Renin and Human Angiotensinogen Genes, J Clin Invest, 97(4):1047-1055 (1996).
Moriyama, Y. et al., The Role of V-ATPase in Neuronal and Endocrine Systems, J Exp Biol, 172:171-178 (1992).
Müller, D.N. et al., Prorenin Receptor Regulates More Than the Renin-Angiotensin System, Annals of Medicine, 44(Suppl 1):S43-48 (2012).
Müller, D.N. et al., (Pro)renin Receptor Peptide Inhibitor "Handle-Region" Peptide Does Not Affect Hypertensive Nephrosclerosis in Goldblatt Rats, Hypertension, 51:676-681 (2008).
Myers, E. et al., Optimal Alignments in Linear Space, Cabios, 4:11-17 (1989).
Nabi, A.H. et al., Prorenin has High Affinity Multiple Binding Sites for (Pro )renin Receptor, Biochim Biophys Acta, 1794:1838-1847 (2009).
Nabi, A.H. et al., Binding Properties of Rat Prorenin and Renin to the Recombinant Rat Renin/Prorenin Receptor Prepared by a Baculovirus Expression System, Int J Mol Med, 18:483-488 (2006).
Nakata, T. et al., Paraventricular Nucleus Lesions Attenuate the Development of Hypertension in DOCA/Salt-Treated Rats, Am J Hypertens, 2:625-630 (1989).
Needleman, S.B. et al., A General Method of Applicable to the Search for Similarities in the Amino Acid Sequence of Two Proteins, J Mol Biol, 48: 444-453 (1970).
Nguyen, G. et al.,The Renin Receptor: the Facts, the Promise and the Hope, Curr Opin Nephrol Hypertens, 12(1):51-55 (2003).
Nguyen, G. et al., Physiology and Pharmacology of the (Pro)renin Receptor, Contrepas A Curr Opin Pharmacol, 8:127-132 (2008).
Nguyen, G. et al., The (Pro)renin Receptor: Therapeutic Consequences, Expert Opin Investig Drugs, 15:1131-1135 (2006).
Nguyen, G. et al., Pivotal Role of the Renin/Prorenin Receptor in Angiotensin II Production and Cellular Responses to Renin, J Clin Invest, 109:1417-1427 (2002).
Nguyen, G. et al., The Biology of the (Pro)renin Receptor, J Am Soc Nephrol, 21:18-23 (2010).
Nguyen, G. et al., The (Pro)renin Receptor: Pathophysiological Roles in Cardiovascular and Renal Pathology, Curr Opin Nephrol Hypertens, 16:129-133 (2007).
Nguyen, G. et al., Renin and Prorenin Receptor in Hypertension: What's New?, Curr Hypertens Rep, 13:79-85 (2011).
Nguyen, G.et al., Plasma Soluble (Pro)renin Receptor is Independent of Plasma Renin, Proreninm and Aldosterone Concentrations But is Affected by Ethnicity, Hypertension 63:297-302 (2014).
Nishimura, M. et al., Benzamil Blockade of Brain Na+ Channels Averts Na+-Induced Hypertension in Rats, Am Physiol Soc, 274:R635-644 (1998).
Osborn, J.W. et al., Circulating Angiotensin II and Dietary Salt: Converging Signals for Neurogenic Hypertension, Curr Hypertens Rep, 9:228-235 (2007).
Oshima, Y. et al., Prorenin Receptor is Essential for Normal Podocyte Structure and Function, J Am Soc Nephrol, 22:2203-2212 (2011).
Ott, C. et al., Association of (*Pro*)*renin* Receptor Gene Polymorphism with Blood Pressure in Caucasian Men, Pharmacogenet, 21:347-349 (2011).
Paliege, A. et al., Inhibition of nNOS Expression in the Macula Densa by COX-2-Derived Prostaglandin $E_2$, Am J Physiol Renal Physiol, 287:F152-159 (2004).
Palmer, L.G. et al., Regulation and Sysregulation of Epithelial Na+ Channels, Clin Exp Nephrol, 16:35-43 (2012).

(56) References Cited

OTHER PUBLICATIONS

Paton, J.F. et al., Neurogenic Hypertension, Exp Physiol, 95:569-571 (2010).
Paul, M. et al., The renin-Angiotensin System in the Brain: Localization and Functional Significance, Arzneim.-Forsch./Drug Res., 43:207-213 (1993).
Paul, M. et al., Physiology of Local Renin-Angiotensin Systems, Physiol Rev, 86:747-803 (2006).
Prieto, M.C. et al., Evolving concepts on regulation and function of renin in distal nephron, Pflugers Arch, 465: 121-13 2. 132 (2013).
Prieto-Carrasquero, M.C. et al., Collecting Duct Renin: A Major Player in Angiotensin II-Dependent Hypertension, J Am Soc Hypertens, 3:96-104 (2009).
Prieto-Carrasquero, M.C. et al., Enhancement of Collecting Duct Renin in Angiotensin II-Dependent Hypertensive Rats, Hypertension, 44:223-229 (2004).
Prieto-Carrasquero, M.C. et al., $AT_1$ Receptor-Mediated Enhancement of Collecting Duct Renin in Angiotensin II-Dependent Hypertensive Rats, Am J Physiol Renal Physiol, 289:F632-637 (2005).
Primatesta, P. et al., Improved Hypertension Management and control: Results from the Health Survey for England 1998, Hypertension, 38:827-832 (2001).
Rademaker, M.T. et al., Hemodynamic, Hormonal, and Renal Effects of (Pro)Renin Receptor Blockade in Experimental Heart Failure, Circ Heart Fail, 5:645-652 (2012).
Radin, M.J. et al., Salt-Induced Cardiac Hypertrophy is Independent of Blood Pressure and Endothelin in Obese, Heart Failure-Prone SHHF Rats, Clin Exp Hypertens, 30:541-552 (2008).
Raizada, M.K. et al., ACE2: A New Target for Cardiovascular Disease Therapeutics, J Cardiovasc Pharmacol, 50:112-119 (2007).
Riediger, F. et al., Prorenin Receptor is Essential for Podocyte Autophagy and Survival, J Am Soc Nephrol, 22:2193-2202 (2011).
Ringholm, L. et al., A high concentration of pro renin in early pregnancy is associated with development of pre-eclampsia in women with type 1 diabetes, Diabetologia, 54:1615-1619 (2011).
Saris, J.J. et al., Prorenin Induces Intracellular Signaling in Cardiomyocytes Independently of Angiotensin II, Hypertension, 48:564 571 (2006).
Satofuka, S. et al., (Pro)renin Receptor Promotes Choroidal Neovascularization by Activating Its Signal Transduction and Tissue Renin-Angiotensin System, Am J Pathol, 173:1911-1918 (2008).
Schenk, J. et al., The Pathogenesis of DOCA-Salt Hypertension, J Pharmacol Toxicol Methods, 27:161-170 (1992).
Sealey, I.E. et al., Plasma prorenin in first-trimester pregnancy: Relationship to changes in human chorionic gonadotropin, Am J Obstet Gynecol, 153:514-519 (1985).
Seki, Y. et al., 2010. Add-on blockade of (pro)renin receptor in imidapril-treated diabetic SHRsp, Front Biosci E2:972-979 (2010).
Shan, Z. et al., Involvement of the Brain (Pro)renin Receptor in Cardiovascular Homeostasis, Circ Res, 107:934-938 (2010).
Shan, Z. et al., Characterization of a Functional (Pro)renin Receptor in Rat brain Neurons, Exp Physiol, 93 :701-708 (2008).
Shi, P. et al., Organum Vasculosum Lamine Terminalis Contributes to Increased Sympathetic Nerve Activity Induced by Central Hypersmolality, Am J Physio Regul Integr Comp Physiol, 293:R2279-R2289 (2007).
Siragy, H.M. et al., Renal (Pro)renin Receptor Upregulation in Diabetic Rats Through Enhanced Angiotensin $AT_1$ Receptor and NADPH Oxidase Activity, Exp Physiol, 93:709-714 (2008).
Sun, P. et al., Angiotensin II stimulates epithelial sodium channels in the cortical collecting duct of the rat kidney, Am J Physiol Renal Physiol 302:F679-687 (2012).
Takahashi, K. et al., Expression of (Pro)renin Receptor in the Human Brain and Pituitary, and Co-localisation with Arginine Vasopressin and Oxytocin in the Hypothalamus, J Neuroendocrinol, 22:453-459 (2010).
te Riet, L. et al., Deterioration of kidney function by the (pro)renin receptor blocker handle region peptide in aliskiren-treated diabetic transgenic (mRen2)27 rats, Am J Physiol Renal Physiol, 306:F1179-1189 (2014).
Thompson, M.W. et al., Regulation of Human Renin mRNA Expression and Protein Release in Transgenic Mice, Hypertension, 28:290-296 (1996).
Toney, G.M. et al., Hypersmotic Activation of CNS Sympathetic Drive: Implications for Cardiovascular Disease, J Physiol, 588:3375-3384 (2010).
van Esch, J.H. et al., Handle region Peptide Counteracts the Beneficial Effects of the Renin Inhibitor Aliskiren in Spontaneously Hypertensive Rats, Hypertension, 57:852-858 (2011).
Wang, F. et al., Prostaglandin E-Prostanoid$_4$ Receptor Mediates Angiotensin II-Induced (Pro)Renin Receptor Expression in the Rat Renal Medulla, Hypertension, 64:369-377 (2014).
Wang, F. et al., COX-2 Mediates Angiotensin II-Induced (Pro)Renin Receptor Expression in the Rat Renal Medulla, Am J Physiol Renal Physiol, 307:F25-F32 (2014).
Watanabe, N. et al., Soluble (Pro)renin Receptor and Blood Pressure During Pregnancy: A Prospective Cohort Study, Hypertension 60:1250-1256 (2012).
Watanabe, N. et al., Prediction of Gestational Diabetes Mellitus by Soluble (Pro)renin Receptor During the First Trimester,J Clin Endocrinol Metab, 98:2528-2535 (2013).
Wei, S.G., et al., Systemically Administered Tempol Reduces Neuronal Activity in Paraventricular nucleus of Hypothalamus and Rostral Ventrolateral Medulla in Rats, J Hypertens, 27:543-550 (2009>.
Wilkinson-Berka, J.L. et al., RILLKKMPSV Influences the Vasculature, Neurons and Glia, and (Pro)renin Receptor Expression in the Retina, Hypertension, 55:1454-1460 (2010).
Xia, H. et al., $ACE_2$ Expression in the Central Nervous System Reduces Angiotensin-II-Mediated Hypertension and Cardiac Hypertrophy in Transgenic Mice, FASEB J, 22: 1236 (2008).
Xu, H. et al., Increased Sympathetic Venoconstriction and Reactivity to Norepinephrine in Mesenteric Veins in Anesthetized DOCA-Salt Hypertensive Rats, Am J Physiol Heart Circ Physiol, 293:H160-H168 (2007).
Xu, P. et al., ACE2/ANG-(1-7)/Mas Pathway in the Brain: The Axis of Good, Am J Physiol Regul Integr Comp Physiol, 300:R804-R817 (2010).
Yang, T. et al., Influence of genetic background and gender on hypertension and renal failure in COX-2-deficient mice, Am J Physiol Renal Physiol, 288:F1125 1132 (2005).
Yemane, H. et al.,Neurohumoral Mechanisms in Deoxycorticosterone Acetate (DOCA)-Salt Hypertension Rats, Exp Physiol, 95:51-55 (2009).
Yokota, H. et al., Higher levels of prorenin predict development of diabetic retinopathy in patients with type 2 diabetes, J Renin Angiotensin Aldosterone Syst, 12:290-294 (2011).
Yoshikawa, A. et al., The (pro)renin receptor is cleaved by ADAM19 in the Golgi leading to its secretion into extracellular space, Hypertens Res, 34:599-605 (2011).
Yusuf, S. et al., Effects of an Angiotensin-Converting-Enzyme Inhibitor, Ramipril, on Cardiovascular Events in High-Risk Patients, New Engl J Med, 342-145-153 (2000).
Zhang, J. et al., Hydrogen Sulfide Prevents Hydrogen Peroxide-Induced Activation of Ephithelial Sodium Channel Through a PTEN/PI(3,4,5)$P_3$ Dependent Pathway, PLoS One 8(5):e64304 (2013).
Zimmerman, M.C. et al., Hypertension Caused by Angiotensin II Infusion Involves Increased Superoxide Production in the Central Nervous System, Circ Res, 95:210-216 (2004).
Zubcevic, J. et al., Autonomic-Immune-Vascular Interaction: An Emerging Concept for Neurogenic Hypertension, Hypertension, 57: 1026-1033 (2011).
International Preliminary Report on Patentability issued Mar. 24, 2015 by the International Searching Authority for Itnernational Patent Application No. PCT/US2013/060437, which was published as WO 2014/047194 on Mar. 27, 2014 (Inventor-Feng; Applicant-Univ. of Utah Research Foundation) (11 pages).

(56) References Cited

OTHER PUBLICATIONS

International Search Report and Written Opinion mailed Jan. 10, 2014 by the International Searching Authority for International Patent Application No. PCT/US2013/060437, which was published as WO 2014/047194 on Mar. 27, 2014 (Inventor-Feng; Applicant-Univ. of Utah Research Foundation) (18 pages).
Notice of Abandonment issued Apr. 10, 2015 for U.S. Appl. No. 14/032,176, which was published as US 2014/0094409 on Apr. 3, 2014 (Inventor-Yeng; Applicant-Univ. of Utah Research Foundation) (2 pages).
Non-Final Office Action issued Aug. 14, 2014 by the U.S. Patent & Trademark Office for U.S. Appl. No. 14/032,176, which was published as US 2014/0094409 on Apr. 3, 2014 (Inventor-Feng; Applicant-Univ. of Utah Research Foundation) (25 pages).
Preliminary Amendment Filed on Oct. 13, 2014 for U.S. Appl. No. 14/449,714, filed Aug. 1, 2014 and published as US 2015/0025013 on Jan. 22, 2015 (Inventor-Feng; Applicant-Univ. Utah Research Foundation) (7 pages).
Restriction Requirement issued on May 22, 2015 by the U.S. Patent & Trademark Office for U.S. Appl. No. 14/499,714, filed Aug. 1, 2014 and published as US 2015/0025013 on Jan. 22, 2015 (Inventor-Feng; Applicant-Univ. Utah Research Foundation) (9 pages).

\* cited by examiner

SEQ ID No. 7

AA sequence: L P Abu D Dht Dht A F K R I F A K R A P Dha I
                        |_____S_____|       |___S___|

Chemical structure:

SEQ ID No. 8
    PR203
        AA sequence: K R I F A K R A P Dha I
                             └──S──┘

FIG. 20

PR30 (SEQ ID NO: 16):
AA sequence: L P T D T I I F K R I F L K R M P S I R E

PR301 (SEQ ID NO: 18):
AA sequence: L P Dhb D Abu Dhb Dhb F Ala R I F L K R M P Dhb I R E
                              |_____S_____|

P

PR40 (SEQ ID NO: 17):
AA sequence: L P _I_ T _R_ T A T _F_ E _R_ _I_ P L K K M P _S_ V R E PR401 (SEQ ID NO: 21):
AA sequence: L P Dhb R Abu A Dhb F Ala—R I P L K K M P Dha V R E

S

PR402 (SEQ ID NO: 22):

AA sequence: L P Dhb R Dhb A Dhb F K R I P L K K M P Ala V R Ala

S

PR403 (SEQ ID NO: 23):

AA sequence: L P Dhb R Abu A Dhb F Ala R I P L K K M P Ala V R Ala

S S

*FIG. 22*

```
SEQUENCE LISTING

<160> NUMBER OF SEQ ID NOS: 23

<210> SEQ ID NO 1
<211> LENGTH: 16
<212> TYPE: PRT
<213> ORGANISM: Artificial Sequence
<220> FEATURE:
<223> OTHER INFORMATION: PRR antagonist peptide (PR10)

<400> SEQUENCE: 1

Ile Phe Asp Asn Ile Ile Ser Gln Gly Val Leu Lys Glu Asp Val Phe
1               5                   10                  15

<210> SEQ ID NO 2
<211> LENGTH: 19
<212> TYPE: PRT
<213> ORGANISM: Artificial Sequence
<220> FEATURE:
<223> OTHER INFORMATION: PRR antagonist peptide (PR20)

<400> SEQUENCE: 2

Leu Pro Thr Asp Thr Thr Thr Phe Lys Arg Ile Phe Leu Lys Arg Met
1               5                   10                  15

Pro Ser Ile

<210> SEQ ID NO 3
<211> LENGTH: 16
<212> TYPE: PRT
<213> ORGANISM: Artificial Sequence
<220> FEATURE:
<223> OTHER INFORMATION: Modified PRR antagonist peptide (PR103)
<220> FEATURE:
<221> NAME/KEY: THIOETH
<222> LOCATION: (4)..(8)
<220> FEATURE:
<221> NAME/KEY: MOD_RES
<222> LOCATION: (7)..(7)
<223> OTHER INFORMATION: Xaa = dehydroalanine (Dha)

<400> SEQUENCE: 3

Ile Phe Asp Ala Ile Ile Xaa Ala Gly Val Leu Lys Glu Asp Val Phe
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Modified PRR antagonist peptide (PR105)
<220> FEATURE:
<221> NAME/KEY: THIOETH
<222> LOCATION: (3)..(6)
```

```
<220> FEATURE:
<221> NAME/KEY: MOD_RES
<222> LOCATION: (7)..(7)
<223> OTHER INFORMATION: Xaa = Dehydroalanine (Dha)
<220> FEATURE:
<221> NAME/KEY: THIOETH
<222> LOCATION: (11)..(14)

<400> SEQUENCE: 4

Ile Phe Ala Asn Ile Ala Xaa Gln Gly Val Ala Lys Glu Ala Val Phe
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Modified PRR antagonist peptide (PR107)
<220> FEATURE:
<221> NAME/KEY: THIOETH
<222> LOCATION: (4)..(8)
<220> FEATURE:
<221> NAME/KEY: MOD_RES
<222> LOCATION: (7)..(7)
<223> OTHER INFORMATION: Xaa = Dehydroalanine (Dha)
<220> FEATURE:
<221> NAME/KEY: THIOETH
<222> LOCATION: (11)..(14)

<400> SEQUENCE: 5

Ile Phe Asp Ala Ile Ile Xaa Ala Gly Val Ala Lys Glu Ala Val Phe
1               5                   10                  15

<210> SEQ ID NO 6
<211> LENGTH: 19
<212> TYPE: PRT
<213> ORGANISM: Artificial Sequence
<220> FEATURE:
<223> OTHER INFORMATION: Modified PRR antagonist peptide  (PR201)
<220> FEATURE:
<221> NAME/KEY: MOD_RES
<222> LOCATION: (3)..(3)
<223> OTHER INFORMATION: Abu
<220> FEATURE:
<221> NAME/KEY: THIOETH
<222> LOCATION: (3)..(6)
<220> FEATURE:
<221> NAME/KEY: MOD_RES
<222> LOCATION: (5)..(5)
<223> OTHER INFORMATION: Xaa = Dehydrobutyrine (Dhb)
<220> FEATURE:
<221> NAME/KEY: MOD_RES
<222> LOCATION: (7)..(7)
<223> OTHER INFORMATION: Abu
<220> FEATURE:
<221> NAME/KEY: THIOETH
<222> LOCATION: (7)..(11)
<220> FEATURE:
<221> NAME/KEY: THIOETH
<222> LOCATION: (13)..(16)
<220> FEATURE:
<221> NAME/KEY: MOD_RES
<222> LOCATION: (18)..(18)
<223> OTHER INFORMATION: Xaa = Dehydroalanine (Dha)

<400> SEQUENCE: 6

Leu Pro Xaa Asp Xaa Ala Xaa Phe Lys Arg Ala Phe Ala Lys Arg Ala
1               5                   10                  15

Pro Xaa Ile

<210> SEQ ID NO 7
<211> LENGTH: 19

```
<212> TYPE: PRT
<213> ORGANISM: Artificial Sequence
<220> FEATURE:
<223> OTHER INFORMATION: Modified PRR antagonist peptide (PR202)
<220> FEATURE:
<221> NAME/KEY: MOD_RES
<222> LOCATION: (3)..(3)
<223> OTHER INFORMATION: Abu
<220> FEATURE:
<221> NAME/KEY: THIOETH
<222> LOCATION: (3)..(7)
<220> FEATURE:
<221> NAME/KEY: MOD_RES
<222> LOCATION: (5)..(6)
<223> OTHER INFORMATION: Xaa = Dehydrobutyrine (Dhb)
<220> FEATURE:
<221> NAME/KEY: THIOETH
<222> LOCATION: (13)..(16)
<220> FEATURE:
<221> NAME/KEY: MOD_RES
<222> LOCATION: (18)..(18)
<223> OTHER INFORMATION: Xaa = Dehydroalanine (Dha)

<400> SEQUENCE: 7

Leu Pro Xaa Asp Xaa Xaa Ala Phe Lys Arg Ile Phe Ala Lys Arg Ala
1               5                   10                  15

Pro Xaa Ile

<210> SEQ ID NO 8
<211> LENGTH: 11
<212> TYPE: PRT
<213> ORGANISM: Artificial Sequence
<220> FEATURE:
<223> OTHER INFORMATION: Modified PRR antagonist peptide (PR203)
<220> FEATURE:
<221> NAME/KEY: THIOETH
<222> LOCATION: (5)..(8)
<220> FEATURE:
<221> NAME/KEY: MOD_RES
<222> LOCATION: (10)..(10)
<223> OTHER INFORMATION: Xaa = Dehydroalanine (Dha)

<400> SEQUENCE: 8

Lys Arg Ile Phe Ala Lys Arg Ala Pro Xaa Ile
1               5                   10

<210> SEQ ID NO 9
<211> LENGTH: 27
<212> TYPE: DNA
<213> ORGANISM: Artificial Sequence
<220> FEATURE:
<223> OTHER INFORMATION: Primer

<400> SEQUENCE: 9
ttgagtctta aacatacttg aatgacc                                       27

<210> SEQ ID NO 10
<211> LENGTH: 32
<212> TYPE: DNA
<213> ORGANISM: Artificial Sequence
<220> FEATURE:
<223> OTHER INFORMATION: Primer

<400> SEQUENCE: 10 gaactttta tcattttgag tgcctcctta ta                                  32

<210> SEQ ID NO 11
<211> LENGTH: 35
<212> TYPE: DNA
<213> ORGANISM: Artificial Sequence
```

-continued

```
<220> FEATURE:
<223> OTHER INFORMATION: Primer

<400> SEQUENCE: 11
ggcactcaaa atgataaaaa gttcatttaa agctc                              35

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
cttctcattt cctcttccct cc                                            22

<210> SEQ ID NO 13
<211> LENGTH: 27
<212> TYPE: DNA
<213> ORGANISM: Artificial Sequence
<220> FEATURE:
<223> OTHER INFORMATION: Primer

<400> SEQUENCE: 13
ctagtcttat aactatactg acaatag                                       27

<210> SEQ ID NO 14
<211> LENGTH: 22
<212> TYPE: DNA
<213> ORGANISM: Artificial Sequence
<220> FEATURE:
<223> OTHER INFORMATION: Primer

<400> SEQUENCE: 14
tcatttcctc ttccctcctt tc                                            22

<210> SEQ ID NO 15
<211> LENGTH: 40
<212> TYPE: PRT
<213> ORGANISM: Artificial Sequence
<220> FEATURE:
<223> OTHER INFORMATION: Designed NisA leader peptide

<400> SEQUENCE: 15

Met Ser Thr Lys Asp Phe Asn Leu Asp Leu His His His His His
1               5                   10                  15

Asp Ser Gly Ala Ser Pro Arg Ile Thr Ser Ile Ser Leu Cys Thr Pro
            20                  25                  30

Gly Cys Lys Thr Gly Ala Leu Met
        35                  40

<210> SEQ ID NO 16
<211> LENGTH: 21
<212> TYPE: PRT
<213> ORGANISM: Artificial Sequence
<220> FEATURE:
<223> OTHER INFORMATION: PRR antagonist peptide (PR30)

<400> SEQUENCE: 16

Leu Pro Thr Asp Thr Thr Thr Phe Lys Arg Ile Phe Leu Lys Arg Met
1               5                   10                  15

Pro Ser Ile Arg Glu
            20
```

-continued

```
<210> SEQ ID NO 17
<211> LENGTH: 21
<212> TYPE: PRT
<213> ORGANISM: Artificial Sequence
<220> FEATURE:
<223> OTHER INFORMATION: PRR antagonist peptide (PR40)

<400> SEQUENCE: 17

Leu Pro Thr Arg Thr Ala Thr Phe Glu Arg Ile Pro Leu Lys Lys Met
1               5                   10                  15

Pro Ser Val Arg Glu
            20

<210> SEQ ID NO 18
<211> LENGTH: 21
<212> TYPE: PRT
<213> ORGANISM: Artificial Sequence
<220> FEATURE:
<223> OTHER INFORMATION: Modified PRR antagonist peptide (PR301)
<220> FEATURE:
<221> NAME/KEY: MOD_RES
<222> LOCATION: (3)..(3)
<223> OTHER INFORMATION: Xaa = Dehydrobutyrine (Dhb)
<220> FEATURE:
<221> NAME/KEY: MOD_RES
<222> LOCATION: (5)..(5)
<223> OTHER INFORMATION: Abu
<220> FEATURE:
<221> NAME/KEY: THIOETH
<222> LOCATION: (5)..(9)
<220> FEATURE:
<221> NAME/KEY: MOD_RES
<222> LOCATION: (6)..(7)
<223> OTHER INFORMATION: Xaa = Dehydrobutyrine (Dhb)
<220> FEATURE:
<221> NAME/KEY: MOD_RES
<222> LOCATION: (18)..(18)
<223> OTHER INFORMATION: Xaa = Dehydroalanine (Dha)

<400> SEQUENCE: 18

Leu Pro Xaa Asp Xaa Xaa Xaa Phe Ala Arg Ile Phe Leu Lys Arg Met
1               5                   10                  15

Pro Xaa Ile Arg Glu
            20

<210> SEQ ID NO 19
<211> LENGTH: 21
<212> TYPE: PRT
<213> ORGANISM: Artificial Sequence
<220> FEATURE:
<223> OTHER INFORMATION: Modified PRR antagonist peptide (PR302)
<220> FEATURE:
<221> NAME/KEY: MOD_RES
<222> LOCATION: (3)..(3)
<223> OTHER INFORMATION: Xaa = Dehydrobutyrine (Dhb)
<220> FEATURE:
<221> NAME/KEY: MOD_RES
<222> LOCATION: (5)..(7)
<223> OTHER INFORMATION: Xaa = Dehydrobutyrine (Dhb)
<220> FEATURE:
<221> NAME/KEY: THIOETH
<222> LOCATION: (18)..(21)

<400> SEQUENCE: 19

Leu Pro Xaa Asp Xaa Xaa Xaa Phe Lys Arg Ile Phe Leu Lys Arg Met
1               5                   10                  15

Pro Ala Ile Arg Ala
            20

<210> SEQ ID NO 20
```

```
<211> LENGTH: 21
<212> TYPE: PRT
<213> ORGANISM: Artificial Sequence
<220> FEATURE:
<223> OTHER INFORMATION: Modified PRR antagonist peptide (PR303)
<220> FEATURE:
<221> NAME/KEY: MOD_RES
<222> LOCATION: (3)..(3)
<223> OTHER INFORMATION: Xaa = Dehydrobutyrine (Dhb)
<220> FEATURE:
<221> NAME/KEY: MOD_RES
<222> LOCATION: (5)..(5)
<223> OTHER INFORMATION: Abu
<220> FEATURE:
<221> NAME/KEY: THIOETH
<222> LOCATION: (5)..(9)
<220> FEATURE:
<221> NAME/KEY: MOD_RES
<222> LOCATION: (6)..(7)
<223> OTHER INFORMATION: Xaa = Dehydrobutyrine (Dhb)
<220> FEATURE:
<221> NAME/KEY: THIOETH
<222> LOCATION: (18)..(21)

<400> SEQUENCE: 20

Leu Pro Xaa Asp Xaa Xaa Xaa Phe Ala Arg Ile Phe Leu Lys Arg Met
1               5                   10                  15

Pro Ala Ile Arg

```
<221> NAME/KEY: MOD_RES
<222> LOCATION: (5)..(5)
<223> OTHER INFORMATION: Xaa = Dehydrobutyrine (Dhb)
<220> FEATURE:
<221> NAME/KEY: MOD_RES
<222> LOCATION: (7)..(7)
<223> OTHER INFORMATION: Xaa = Dehydrobutyrine (Dhb)
<220> FEATURE:
<221> NAME/KEY: THIOETH
<222> LOCATION: (18)..(21)

<400> SEQUENCE: 22

Leu Pro Xaa Arg Xaa Ala Xaa Phe Lys Arg Ile Pro Leu Lys Lys Met
1               5                   10                  15

Pro Ala Val Arg Ala
            20

<210> SEQ ID NO 23
<211> LENGTH: 21
<212> TYPE: PRT
<213> ORGANISM: Artificial Sequence
<220> FEATURE:
<223> OTHER INFORMATION: Modified PRR antagonist peptide  (PR403)
<220> FEATURE:
<221> NAME/KEY: MOD_RES
<222> LOCATION: (3)..(3)
<223> OTHER INFORMATION: Xaa = Dehydrobutyrine (Dhb)
<220> FEATURE:
<221> NAME/KEY: MOD_RES
<222> LOCATION: (5)..(5)
<223> OTHER INFORMATION: Abu
<220> FEATURE:
<221> NAME/KEY: THIOETH
<222> LOCATION: (5)..(9)
<220> FEATURE:
<221> NAME/KEY: MOD_RES
<222> LOCATION: (7)..(7)
<223> OTHER INFORMATION: Xaa = Dehydrobutyrine (Dhb)
<220> FEATURE:
<221> NAME/KEY: THIOETH
<222> LOCATION: (18)..(21)

<400> SEQUENCE: 23

Leu Pro Xaa Arg Xaa Ala Xaa Phe Ala Arg Ile Pro Leu Lys Lys Met
1               5                   10                  15

Pro Ala Val Arg Ala
            20
```

ANTAGONIST FOR (PRO)RENIN RECEPTOR FOR THE TREATMENT OF HYPERTENSION AND DIABETES

This application claims benefit of priority under 35 U.S.C. §371 of PCT/US2013/06047, filed Sep. 18, 2013, which claims the benefit under 35 U.S.C. §119(e) of U.S. Provisional Patent Application No. 61/703,205 filed Sep. 19, 2012. The contents of the prior international and provisional applications are hereby incorporated by reference herein in their entirety.

FIELD OF THE INVENTION

The disclosure relates to novel (pro)rennin receptor antagonists and use of the antagonists in the treatment of diseases and disorders including hypertension and diabetes.

STATEMENT REGARDING THE SEQUENCE LISTING

The Sequence Listing submitted Mar. 19, 2015 as a text file named "21101_0299U4_Sequence_Listing," created on Mar. 19, 2015, and having a size of 9,607 bytes is hereby incorporated by reference pursuant to 37 C.F.R. §1.52(e)(5).

BACKGROUND OF THE INVENTION

Hypertension is the most important risk factor for cardiovascular (CV) diseases and remains the number one cause of morbidity and mortality for our country. Despite the variety of traditional antihypertensive agents available, the blood pressure of about 40% of patients is still difficult to manage. A major component of drug resistant hypertension is neurogenic hypertension with increased vasomotor/cardiac sympathetic drive and decreased parasympathetic tone. Many studies demonstrate the importance of the brain renin-angiotensin system (RAS) in the development of neurogenic hypertension. Recently, a new component of the brain RAS was discovered and named the (pro)renin receptor (PRR).

PRR promotes Angiotensin II (Ang II) generation and activates both Ang II-dependent and -independent signaling pathways through binding to renin and prorenin. It is now well recognized that Ang II is produced and acts locally in the central nervous system (CNS) and serves a crucial role in CV function. So far, the beneficial effects of RAS blockade have been attributed to the inhibition of the vasoconstriction and hypertrophy-inducing properties of Ang II. Thus, PRR provides a new target to study the effect of the brain RAS in hypertension because it is a novel component of the RAS, controlling the production of the vasoconstrictor Ang II and the hypertrophic signaling pathways through both Ang II-dependent and -independent signaling pathways.

Current antihypertensive agents target RAS components. Examples include angiotensin-converting enzyme (ACE) inhibitors, Ang II type 1 receptor (AT1R) blockers, and direct renin inhibitors. However, all of these compounds cause dramatic increases of plasma renin levels due to the negative feedback loop (decrease of Ang II levels) on renin production. Renin and prorenin directly bind to PRR and can activate signaling pathways independent of Ang II. The clinical relevance of PRR is particularly significant in situations where there are increases in renin and prorenin levels.

The activation of PRR initiates an intracellular signaling pathway involving mitogen-activated protein kinase which increases the synthesis of profibrotic molecules such as plasminogen activator inhibitor-1, fibronectin, collagen and transforming growth factor-$\beta$. These signaling pathways have been shown to directly link to diabetic retinopathy, nephropathy, cardiac hypertrophy, vascular and kidney fibrosis. In addition, prorenin, an activating ligand of PRR, is found at levels one hundred times higher in the plasma of a diabetic patient than the amount of prorenin found in healthy individuals. Several studies indicate that PRR expression was increased in diabetic retinopathy, nephropathy, and in hypertension.

Some peptides have been developed to antagonize prorenin for use in diabetic nephropathy, high salt induced hypertension in mouse and rat models. However, the effects of these peptides remain controversial because several other independent laboratories were not able to replicate the effects of this peptide.

Thioether bridges have been used in modifying small peptides in the past to increase stability. However, there are currently no available compounds or thioether bridge-modified peptides for treating hypertension that act on the (pro)renin receptor.

SUMMARY OF THE INVENTION

The present invention provides (pro)renin receptor antagonist compositions, including novel peptides comprising thioether bridges that stabilize the molecules. Also provided are methods for treating a disease or disorder, e.g., hypertension, with a (pro)renin receptor antagonist. The (pro)renin receptor antagonists described herein both reduce Ang-II generation and prevent Ang II-independent signal activation.

One aspect of the invention provides a polypeptide comprising an amino acid sequence having at least 70% identity to the amino acid sequence set forth in one of SEQ ID NOs:1-8 and 16-23. In one embodiment, the polypeptide comprises an amino acid sequence having at least 80% identity to the amino acid sequence set forth in one of SEQ ID NOs:1-8 and 16-23. In another embodiment, the polypeptide comprises an amino acid sequence having at least 90% identity to the amino acid sequence set forth in one of SEQ ID NOs:1-8 and 16-23. In yet another embodiment, a pharmaceutical composition comprises the polypeptide and a pharmaceutically acceptable carrier.

Another aspect of the invention provides a (pro)renin receptor (PRR) antagonist that blocks prorenin from binding to PRR, wherein the PRR antagonist binds to PRR. In one embodiment, the PRR antagonist is a peptide. In another embodiment, the PRR antagonist peptide comprises amino acid residues 3, 4, 6, 7, and 18 of SEQ ID NO:2. In a related embodiment, the PRR antagonist peptide further comprises amino acid residues 8, 10, and 11 of SEQ ID NO:2.

In yet another embodiment, the PRR antagonist peptide further comprises a non-standard amino acid. In one embodiment, the non-standard amino acid is dehydroalanine, 2-aminobutyric acid, or dehydrobutyrine. In another embodiment, the PRR antagonist peptide comprises a thioether bridge.

One aspect of the invention provides a method for treating or preventing a disease or disorder comprising administering an effective amount of one or more PRR antagonists. In one embodiment, the disease or disorder is hypertension, diabetes, diabetic retinopathy, nephropathy, cardiac hypertrophy, vascular or kidney fibrosis. In another embodiment, the PRR antagonist comprises the polypeptide or the PRR antagonist described above.

Another aspect of the invention provides a method for reducing blood pressure comprising administering a PRR antagonist. In one embodiment, the PRR antagonist is a PRR-binding peptide. In another embodiment, the PRR antagonist comprises amino acid residues 3, 4, 6, 7, and 18 of SEQ ID NO:2. In a related embodiment, the PRR antagonist further comprises amino acid residues 8, 10, and 11 of SEQ ID NO:2. In yet another embodiment, the PRR antagonist comprises a non-standard amino acid. In one embodiment, the non-standard amino acid is dehydroalanine, 2-aminobutyric acid, or dehydrobutyrine. In another embodiment, the PRR antagonist comprises a thioether bridge. In one embodiment, the administering step is oral, intravenous, or intracerebroventricular.

BRIEF DESCRIPTION OF THE DRAWINGS

The following drawings form part of the present specification and are included to further demonstrate certain aspects of the present invention. The invention may be better understood by reference to one or more of these drawings in combination with the description of specific embodiments presented herein.

FIG. 20 is a series of fluorescence microscopy images showing PRR binding in the PR20 alanine replacement assay. Each of the amino acid positions of PR20 was substituted with alanine. PR20 and the alanine substituted peptides were labeled with FITC. Fluorescence indicates binding of the peptide to PRR.

FIG. 21 shows the core amino acid sequence for the PR30 peptide (SEQ ID NO:16) and modified thioether bridge containing peptides PR301 (SEQ ID NO:18), PR302 (SEQ ID NO:19), and PR303 (SEQ ID NO:20). PR301 comprises five non-standard amino acid residues, and PR302 and PR303 each comprise four non-standard amino acid residues.

FIG. 22 shows the core amino acid sequence for the PR40 peptide (SEQ ID NO:17) and modified thioether bridge containing peptides PR401 (SEQ ID NO:21), PR402 (SEQ ID NO:22), and PR403 (SEQ ID NO:23). PR401 comprises four non-standard amino acid residues, and PR402 and PR403 each comprise three non-standard amino acids.

DETAILED DESCRIPTION

Figure 1:
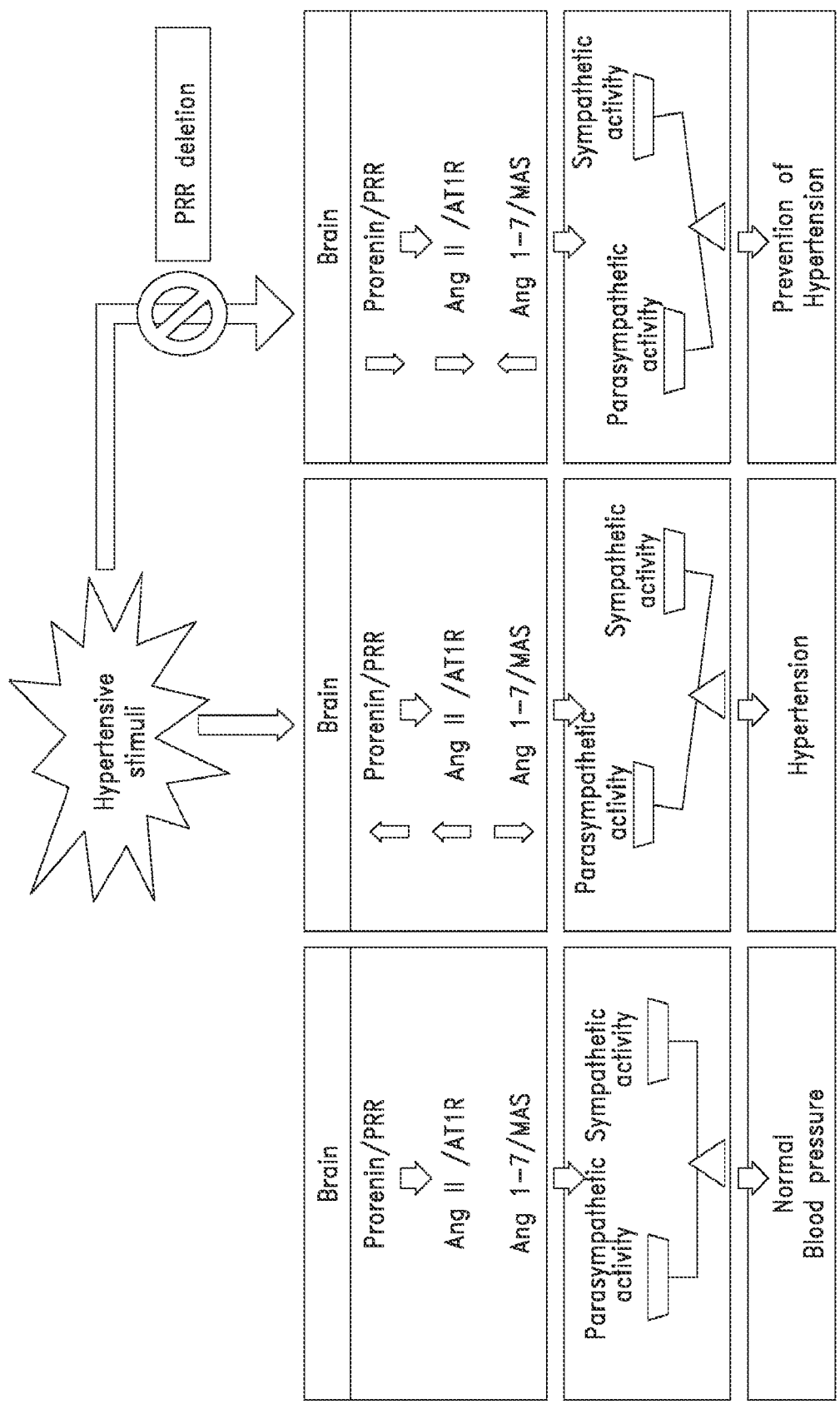
FIG. 1 is a schematic illustrating that hypertensive stimuli increase brain PRR expression, leading to Ang II formation and/or activation of Ang II-independent signaling, and thus hypertension. Therefore deletion of PRR in the brain will mitigate the hypertension.
Figure 2:
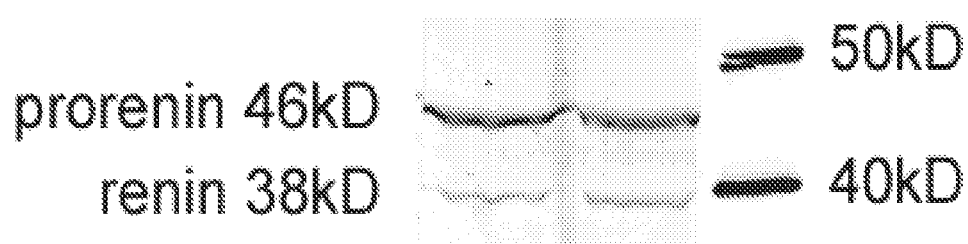
FIG. 2 is an image illustrating prorenin and renin protein expression in brains of C57Bl/6J mice. The prorenin and renin protein was extracted from whole brain lysate. Samples incubated with (pro)renin antibody showed strong bands at 46 kD for prorenin and thin bands at 38 kD for matured renin.
Figure 3:
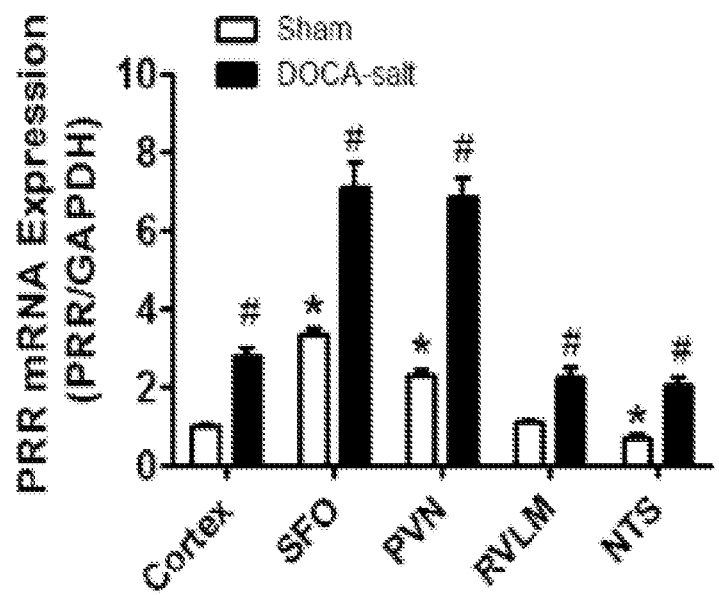
FIG. 3 is a graph illustrating an increase of brain PRR expression in deoxycorticosterone acetate (DOCA)-salt hypertensive mice. The PRR mRNA expression levels varied in CV regulatory regions of the brain and increased following 21 days of DOCA-salt treatment. *$P<0.05$ vs. Sham Cortex; #$P<0.05$ vs. Sham treatment in the same brain nucleus.
Figure 4:
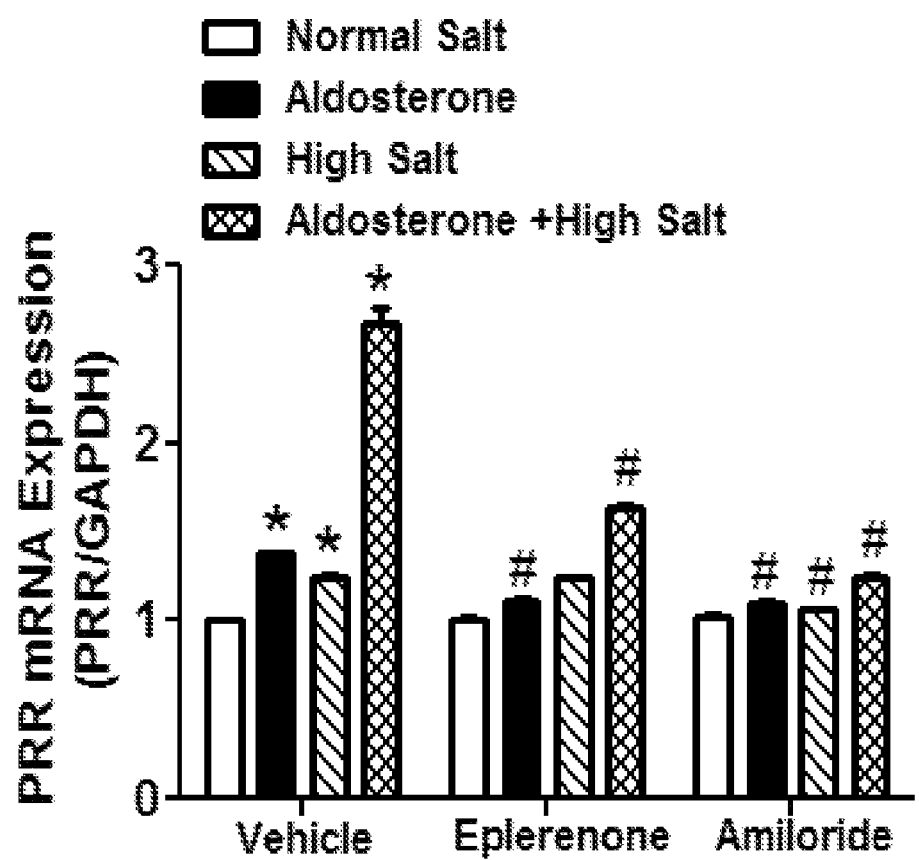
FIG. 4 is a graph illustrating that aldosterone and high salt regulate PRR expression in Neuro-2A cells. Neuro-2A cells were incubated with either normal salt (146 mM) or high salt (160 mM) for 5 days without or with aldosterone (1 μM), MR inhibitor (Eplerenone, 10 μM), or ENaC inhibitor (Amiloride, 10 μM) for 6 hours. *$P<0.05$ vs. normal salt; #$P<0.05$ vs. Vehicle group in the same treatment.

Detailed descriptions of one or more embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in any appropriate manner.

Where ever the phrase "for example," "such as," "including" and the like are used herein, the phrase "and without limitation" is understood to follow unless explicitly stated otherwise. Similarly "an example," "exemplary" and the like are understood to be non-limiting.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c. Where ever the terms "a" or "an" are used, "one or more" is understood, unless such interpretation is nonsensical in context.

As used herein, the term "effective amount" is intended to encompass contexts such as a pharmaceutically effective amount or therapeutically effective amount. For example, in certain embodiments, the effective amount is capable of achieving a beneficial state, beneficial outcome, functional activity in a screening assay, or improvement of a clinical condition.

The terms "polypeptide," "protein" and "peptide" are used interchangeably and mean a polymer of amino acids not limited to any particular length. The term does not exclude modifications such as myristylation, sulfation, glycosylation, phosphorylation and addition or deletion of signal sequences.

The term "antibody" as used herein includes monoclonal antibodies, polyclonal antibodies, multispecific antibodies (e.g., bispecific antibodies), and antibody fragments, so long as they exhibit the desired biological activity, e.g., specifically bind to PRR. The term "immunoglobulin" (Ig) is used interchangeably with "antibody" herein. Monoclonal or polyclonal antibodies specifically reacting with PRR may be made by methods known in the art, and are commercially available. See, e.g., Harlow and Lane (1988) Antibodies: A Laboratory Manual, Cold Spring Harbor Laboratories; Goding (1986) Monoclonal Antibodies: Principles and Practice, 2d ed., Academic Press, New York; and Ausubel et al. (1999) Current Protocols in Molecular Biology, John Wiley & Sons, Inc., New York.

The term "isolated" refers to a subject PRR antagonist, e.g., a thioether bridge modified PRR antagonist peptide, that has been separated and/or recovered from a component of its natural environment, e.g., a host cell culture environment. In certain embodiments, the isolated protein is substantially free from proteins or polypeptides or other contaminants that would interfere with its use (therapeutic, diagnostic, prophylactic, research or otherwise).

The term "polynucleotide" as referred to herein means single-stranded or double-stranded nucleic acid polymers. In certain embodiments, the nucleotides comprising the polynucleotide can be ribonucleotides or deoxyribonucleotides or a modified form of either type of nucleotide. The term "polynucleotide" specifically includes single and double stranded forms of DNA. As will be also recognized by the skilled artisan, polynucleotides may be single-stranded (coding or antisense) or double-stranded, and may be DNA (genomic, cDNA or synthetic) or RNA molecules.

Standard techniques for cloning, DNA isolation, amplification and purification, for enzymatic reactions involving DNA ligase, DNA polymerase, restriction endonucleases and the like, and various separation techniques are those known and commonly employed by those skilled in the art.

The term "operably linked" means that the components to which the term is applied are in a relationship that allows them to carry out their inherent functions under suitable conditions. For example, a transcription control sequence "operably linked" to a protein coding sequence is ligated thereto so that expression of the protein coding sequence is achieved under conditions compatible with the transcriptional activity of the control sequences.

The term "vector" is used to refer to any molecule (e.g., nucleic acid, plasmid, or virus) used to transfer a polynucleotide sequence to a host cell. The term "expression vector" refers to a vector that is suitable for transformation of a host cell and contains nucleic acid sequences that direct and/or control expression of inserted nucleic acid sequences. Expression includes, but is not limited to, processes such as transcription, translation, and RNA splicing, if introns are present.

Calculations of sequence similarity or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch, (1970, J. Mol. Biol. 48: 444-453) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package, using a NWSgapdna. CMP matrix and a gap weight of 40, 50, 60, 70, or 80 and a length weight of 1, 2, 3, 4, 5, or 6. A particularly preferred set of parameters (and the one that should be used unless otherwise specified) are a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (1989, Cabios, 4: 11-17) which has been incorporated into the ALIGN program (version 2.0), using a PAM120 weight residue table, a gap length penalty of 12 and a gap penalty of 4.

As used herein, "treating" or "treatment" refers to an approach for obtaining beneficial or desired results, including and preferably clinical results. Treatment can involve optionally either the amelioration of symptoms of the disease or condition, or the delaying of the progression of the disease or condition.

As used herein, unless the context makes clear otherwise, "prevention," and similar words such as "prevented," "preventing" etc., indicates an approach for preventing, inhibiting, or reducing the likelihood of, the onset or recurrence of a disease or condition. It also refers to preventing, inhibiting, or reducing the likelihood of, the occurrence or recurrence of the symptoms of a disease or condition, or optionally an approach for delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

(Pro)renin Receptor Antagonists

The present invention is based in part on the finding that blocking the (pro)renin receptor (PRR) reduces Angiotensin II (Ang II) generation and also prevents Ang II-independent signal activation. Accordingly, one aspect of the invention relates to PRR antagonists. PRR antagonists include, e.g., small molecule compounds, antisense polynucleotides, polypeptides, including PRR-binding peptides, and anti-PRR antibodies.

A PRR antagonist inhibits or blocks the ligand-receptor interaction of prorenin to PRR. In one embodiment, a PRR antagonist blocks prorenin from binding PRR. In another embodiment, a PRR antagonist competes with prorenin for binding to PRR.

In one embodiment, a polynucleotide variant of a PRR antagonist is provided. A polynucleotide variant may have substantial identity to a PRR antagonist polynucleotide sequence described herein. For example, a polynucleotide may be a polynucleotide comprising at least 70% sequence identity, preferably at least 75%, 80%, 85%, 90%, 95%, 96%, 97%, 98%, or 99% or higher, sequence identity compared to a reference polynucleotide sequence, using the methods described herein, (e.g., BLAST analysis using standard parameters).

In another embodiment, a polypeptide variant of a PRR antagonist is provided. A peptide variant may have substantial identity to a PRR antagonist peptide sequence described herein. For example, a peptide variant may be a peptide comprising at least 70% sequence identity, preferably at least 75%, 80%, 85%, 90%, 95%, 96%, 97%, 98%, or 99% or higher, sequence identity compared to a PRR antagonist peptide described herein.

PRR Antagonist Peptides

In one embodiment of the invention, the PRR antagonist is a peptide that inhibits the binding of prorenin to PRR. Examples of functional PRR antagonist peptides include the peptides disclosed herein, PR10, PR20, PR30, and PR40, with sequences IFDNIISQGVLKEDVF (SEQ ID NO:1), LPTDTTTFKRIFLKRMPSI (SEQ ID NO:2), LPTDTTTFKRIFLKRMPSIRE (SEQ ID NO:16), and LPTRTATFERIPLKKMPSVRE LPTRTATFERIPLK-KMPSVRE (SEQ ID NO:17), respectively. Administration of either PR10 or PR20 intracerebroventricularly (ICV) was shown to significantly reduce prorenin (PR) induced pressor response as described further in the Examples below.

One embodiment of the invention provides a polynucleotide sequence encoding a PRR antagonist peptide. In one embodiment, the polynucleotide is codon optimized for expression in the host cell, e.g., *Lactococcus lactis*. The polynucleotide sequence encoding the PRR antagonist peptide may be part of a construct. Accordingly, the polynucleotide sequence encoding the PRR antagonist peptide may be contained in a vector, such as an expression vector for expression and production by a host cell, e.g., *L. lactis*.

PRR antagonist peptides include modified peptides, e.g., peptides comprising a thioether bridge and/or amino acids that are not standard or naturally occurring in humans, e.g., amino acids found in polypeptides of microbial origin. Examples of non-standard amino acids include, but are not limited to, dehydroalanine (Dha), 2-aminobutyric acid (Abu), and dehydrobutyrine (referred to herein interchangeably as "Dht" or "Dhb").

Figure 18:
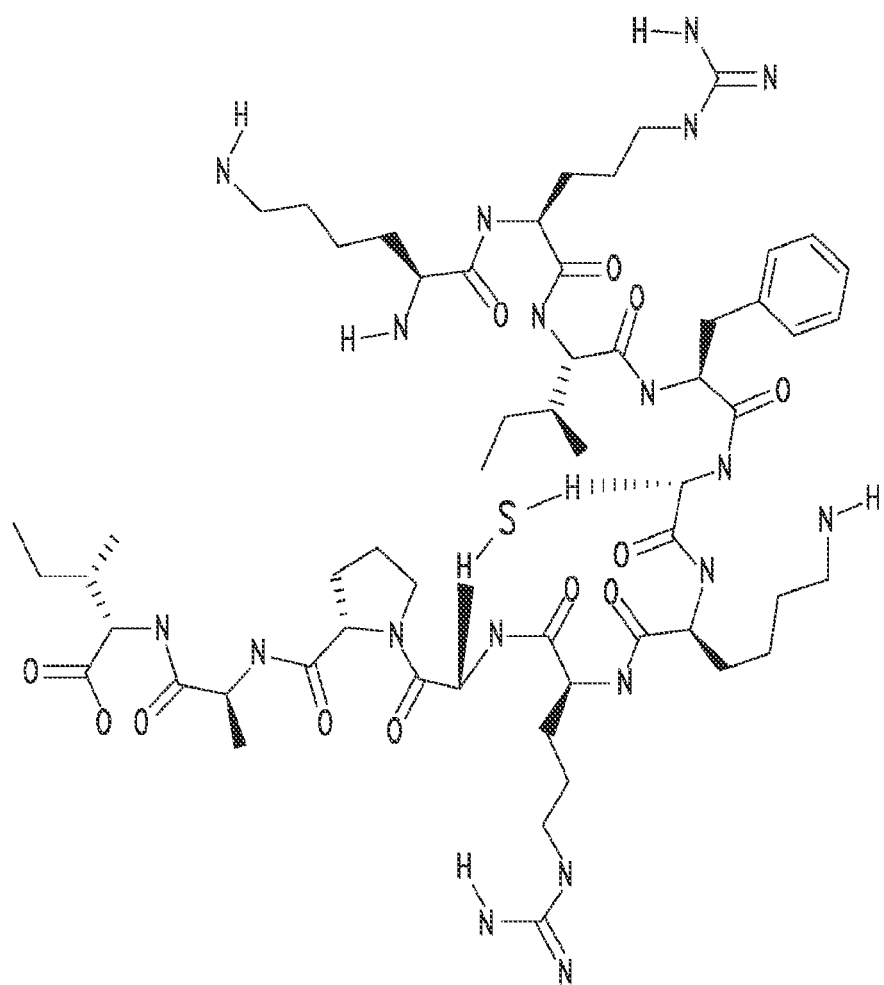
FIG. 18 shows the amino acid sequence and chemical structure of modified peptide PR203 (SEQ ID NO:8) with two thioether bridges and one non-standard amino acid, dehydroalanine (Dha, at position 10).
Figure 19A:
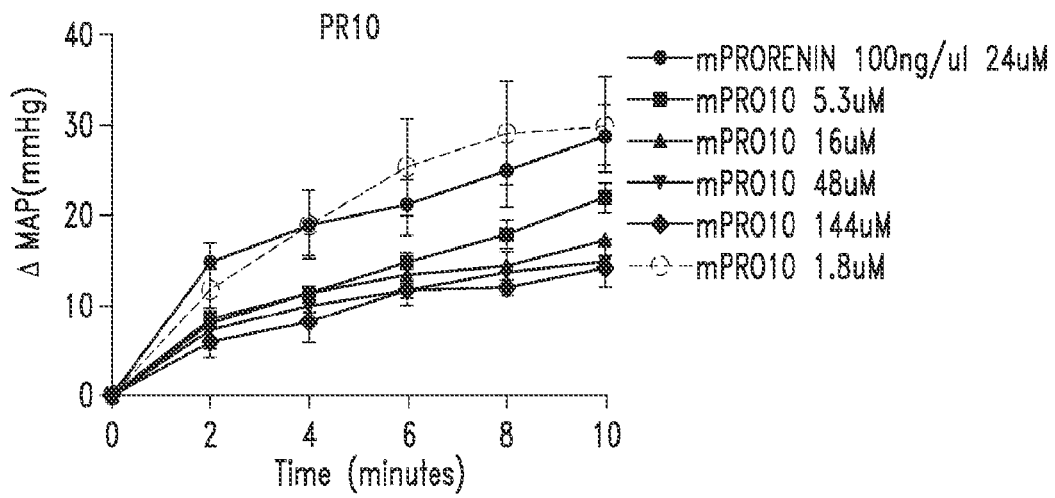
FIG. 19 is a series of graphs showing the exemplary dose responses for peptide PR10 and PR20.
Figure 19B:
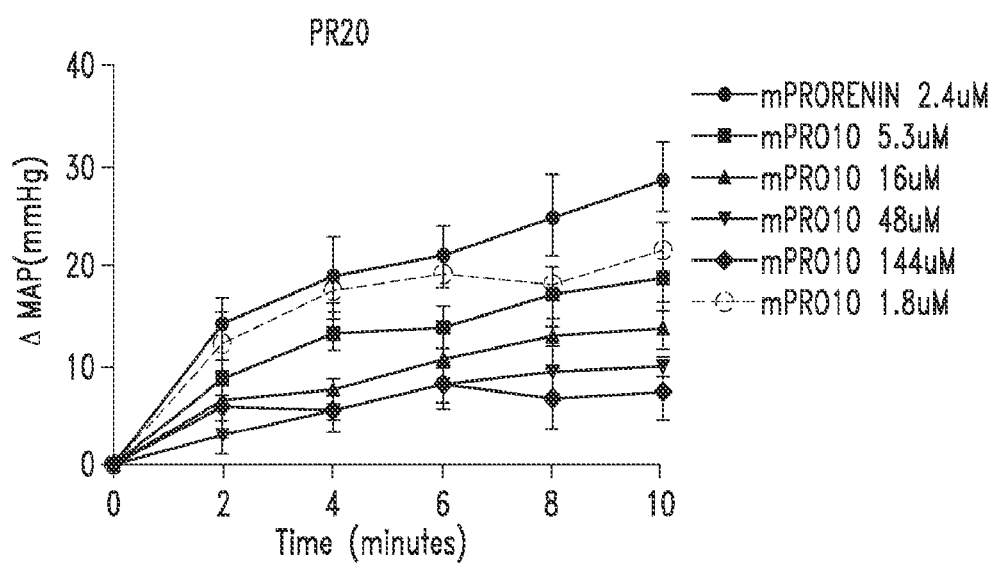

In one embodiment, thioether-bridge modified peptides are designed based on the core amino acid sequences of PR10, PR20, PR30, and PR40 in order to avoid peptide degradation by peptidase in vivo. The introduction of one or more thioether bridges makes the resulting peptides more stable and, therefore, strong PRR antagonists. The NisBTC encoding plasmid (pTU-BTC) and substrate-peptide-encoding plasmids (pPR103, pPR105, pPR107, pPR201, pPR202) were constructed and introduced into the lactic acid producing bacterium *L. lactis* to produce the thioether-bridge containing peptides PR103 (SEQ ID NO:3), PR105 (SEQ ID NO:4), PR107 (SEQ ID NO:5), PR201 (SEQ ID NO:6) and PR202 (SEQ ID NO:7) respectively. One alternative embodiment is PR203 (SEQ ID NO:8) as provided in FIG. 18.

In one embodiment, a PRR antagonist peptide comprises common amino acid substitutions or modifications. For example, a PRR antagonist peptide derived from the core amino acid sequence of PR20 comprises amino acid residues 3, 4, 6, 7, and 18 of the amino acid sequence set forth in SEQ ID NO:2. In a related embodiment, the PRR antagonist peptide derived from PR20 further comprises amino acid residues 8, 10, and 11 of SEQ ID NO:2. In another embodiment, a PRR antagonist peptide comprises amino acid residues 3, 4, 6, 7, and 18 of one of SEQ ID NOs:18-23. In a related embodiment, the PRR antagonist peptide further comprises amino acid residues 8, 10, 11, and 14 of one of SEQ ID NOs:18-23.

In one embodiment, the PRR antagonist is a peptide comprising an amino acid sequence having at least 50% identity to an amino acid sequence set forth in one of SEQ ID NOs:4-8 and 18-23. In another embodiment, the PRR antagonist is a peptide comprising an amino acid sequence having at least 60% identity to an amino acid sequence set forth in one of SEQ ID NOs:4-8 and 18-23. In yet another embodiment, the PRR antagonist is a peptide comprising an amino acid sequence having at least 70% identity to an amino acid sequence set forth in one of SEQ ID NOs:4-8 and 18-23. In one embodiment, the PRR antagonist is a peptide comprising an amino acid sequence having at least 80% identity to an amino acid sequence set forth in one of SEQ ID NOs:4-8 and 18-23. In one embodiment, the PRR antagonist is a peptide comprising an amino acid sequence having at least 90% identity to an amino acid sequence set forth in one of SEQ ID NOs:4-8 and 18-23. In another embodiment, the PRR antagonist is a peptide comprising the amino acid sequence set forth in one of SEQ ID NOs:4-8 and 18-23.

Methods of Use

One aspect of the invention provides a more efficient hypertension treatment because of the dual beneficial effect of PRR blockade that both reduces Ang II generation and prevents Ang II-independent signal activation. The result of PRR deletion mimics the effect of PRR antagonism in hypertension. Deletion of PRR attenuates blood pressure in chronic hypertension and prevents development of hypertension. As described in the examples, intracerebroventricular (ICV) administration of either PR10 or PR20 significantly reduced the prorenin (ICV) induced pressor response in C57Bl/6J mice. Accordingly, the significant reduction in the prorenin-induced pressor response indicated a functional activity of PR10 and PR20 in blocking the effects of prorenin/PRR activation.

In one embodiment, the PRR antagonist is administered to a patient for the treatment or prevention of a disease or disorder including, e.g., hypertension, diabetes, diabetic retinopathy, nephropathy, cardiac hypertrophy, vascular and kidney fibrosis. In certain embodiments, the disease or disorder is chronic hypertension or RAS-dependent hypertension. In one embodiment, the hypertension is neurogenic hypertension.

In another embodiment, the PRR antagonist is used in the preparation of a medicament for the treatment or prevention of a disease or disorder. In one embodiment, the PRR antagonist is a PRR-binding peptide. In a preferred embodiment, the PRR antagonist is a modified peptide. In one embodiment, the modified peptide PRR antagonist comprises one or more thioether bridges. For example, the modified peptide PRR antagonist may comprise one, two, three, or more thioether bridges.

Pharmaceutical Compositions

Pharmaceutical compositions can be made using the PRR antagonists described herein. An effective amount of a therapeutic composition is the minimum dose that produces a measurable effect in a subject, e.g., produces a statistically significant reduction in blood pressure. Pharmaceutical compositions are readily prepared by one of ordinary skill in the art.

A PRR antagonist of the present invention can be lyophilized for storage or formulated into various solutions known in the art for solubility and stability and consistent with safe administration into animals, including humans.

Administration of the PRR antagonists described herein, in pure form or in an appropriate pharmaceutical composition, can be carried out via any of the accepted modes of administration of agents for serving similar utilities. The pharmaceutical compositions can be prepared by combining a PRR antagonist or antagonist-containing composition with an appropriate physiologically acceptable carrier, diluent or excipient, and may be formulated into preparations in solid, semi solid, liquid or gaseous forms, such as tablets, capsules, powders, granules, ointments, solutions, suppositories, injections, inhalants, gels, microspheres, and aerosols. In addition, other pharmaceutically active ingredients (including other anti-hypertensive agents) and/or suitable excipients such as salts, buffers and stabilizers may, but need not, be present within the composition.

"Carriers" as used herein include pharmaceutically or physiologically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as polysorbate 20 (TWEEN™) polyethylene glycol (PEG), and poloxamers (PLURONICS™), and the like.

Administration may be achieved by a variety of different routes, including oral, parenteral, nasal, intravenous, intradermal, subcutaneous or topical. In one embodiment, the PRR antagonist is administered intracerebroventricularly (ICV). In another embodiment, the PRR antagonist is administered orally. Preferred modes of administration depend upon the nature of the condition to be treated or prevented. An amount that, following administration, reduces, inhibits, or prevents hypertension is considered effective.

In particular embodiments, a thioether bridge-modified peptide is designed to be delivered intravenously or orally.

EXAMPLES

The following examples are intended to illustrate but not limit the disclosure. While the disclosure provides certain specific embodiments, the invention is not limited to those embodiments. A person of ordinary skill will appreciate from the description herein that modifications can be made to the described embodiments and therefore that specification is broader in scope than the described embodiments. All examples are therefore non-limiting.

Example 1

Deletion of Prr in the Brain Mitigates Hypertension

Neuron-specific PRR knockout mice (Nefh-PRR) and wildtype (WT) littermates (N=5/group) were each implanted with a telemetric probe for blood pressure (BP) recording and an intracerebroventricular (ICV) cannula for infusion of mouse prorenin (100 ng/ul), mouse renin (100 ng/ul), or an Ang II type 1 receptor (AT1R) blocker (losartan, 10 ug/ul) at 0.3 ul/minute for 10 minutes. Mouse prorenin infusion increased the BP (mmHg) in WT mice ($\Delta$MAP: 41±5); however, the prorenin induced pressor response was abolished in Nefh-PRR mice ($\Delta$MAP: 5±1). Infusion of mouse renin similarly increased BP in Nefh-PRR ($\Delta$MAP: 27±2) and WT ($\Delta$MAP: 31±5) mice. The pressor response induced by prorenin or renin was completely blocked by the infusion of losartan. The data suggest that ICV prorenin, via PRR, mediates Ang II-dependent pressor response in WT mice.

To determine whether PRR contributes to the development of brain RAS-dependent hypertension, Nefh-PRR and WT littermates (N=8/group) were treated with 50 mg of deoxycorticosterone acetate (DOCA) subcutaneously, plus 0.9% NaCl drinking water for 21 days. The baseline BP was similar between Nefh-PRR (101±2) and WT (101±3) mice. BP was increased in WT mice (132±6) by DOCA-salt treatment, while Nefh-PRR mice remained normotensive (108±3).

In summary, prorenin via PRR mediates AngII/AT1R-dependent pressor response in the brain. Neuronspecific PRR deletion attenuates the development of DOCA-salt hypertension likely due to the lack of Ang II/AT1R activation.

Example 2

Blocking PRR Improves Baroreflex Sensitivity and Autonomic Function and is Linked to the Attenuation of DOCA-Salt Hypertension Elevated expression and activity of RAS components in the brain CV control regions support the concept that the brain RAS is involved in the pathogenesis of hypertension, including DOCA-salt hypertension. PRR participates in Ang II generation, triggering both Ang II-dependent and -independent activation of signaling pathways, and plays a significant role in regulating CV function. Accordingly, decreasing PRR expression in CV regulatory nuclei will reduce Ang II generation and/or decrease Ang II-independent signals, resulting in vasodilation and reduction of BP.

Figure 5A:
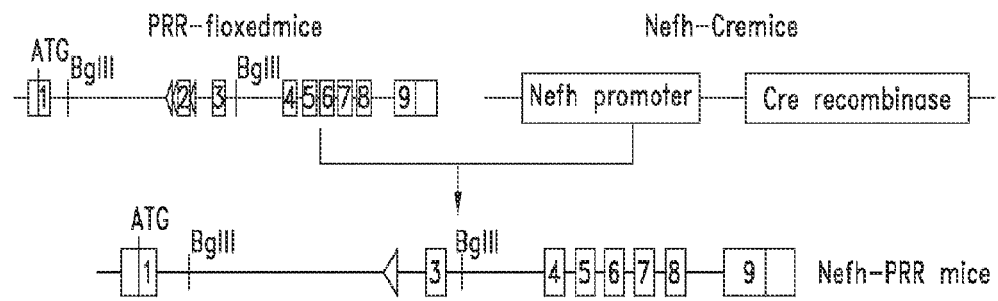
FIG. 5A is a diagram illustrating the PRR gene deleted by Cre recombinase under the control of neurofilament-H promoter in the Nefh-PRR mouse model for brain-targeted PRR deletion.
Figure 5B:
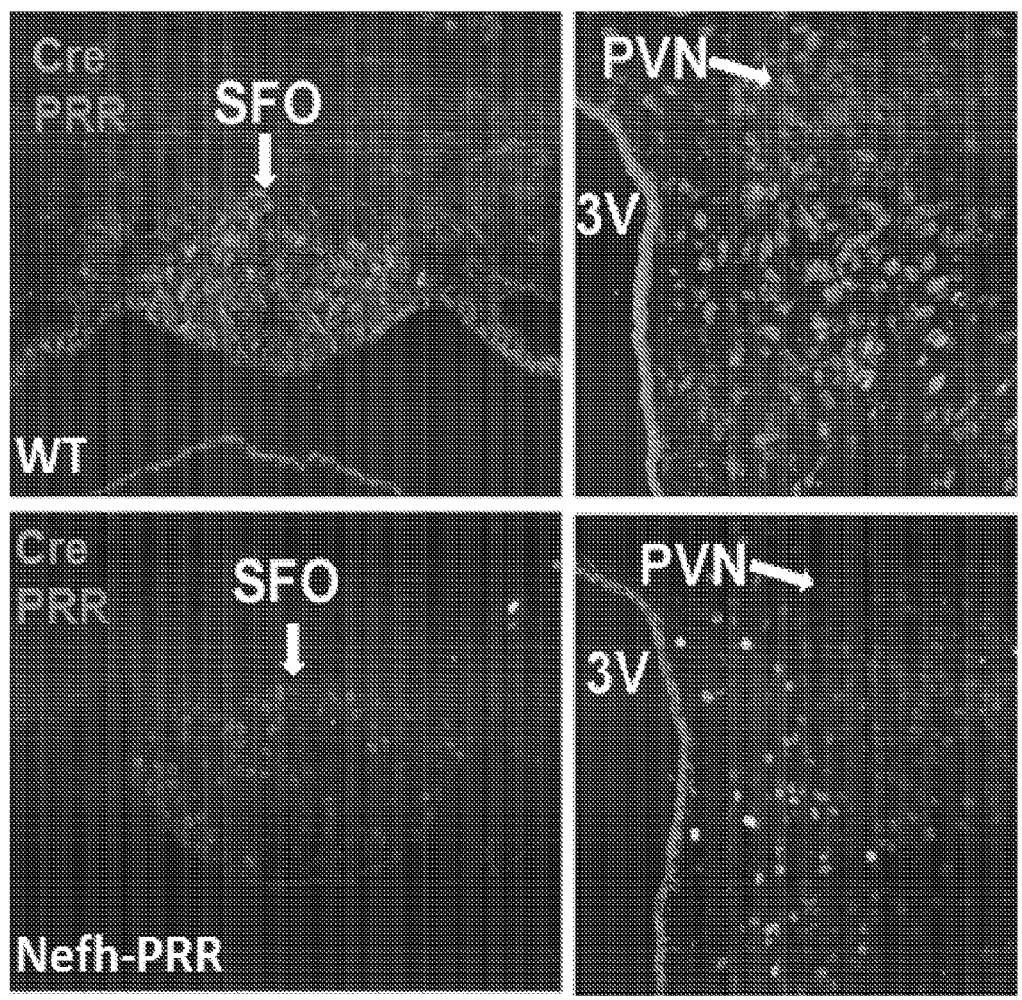
FIG. 5B is a series of representative immuno-fluorescent images of the subfornical organ (SFO) and paraventricular nucleus (PVN) in WT and Nefh-PRR mice.

A conditional PRR knockout mouse model with deletion of PRR specifically in neurons was generated and characterized. The mouse PRR exon 2 gene was deleted by breeding PRR floxed mice with mice that express Cre recombinase under the control of the neuron-specific neurofilament-H (Nefh) promoter (Nefh-Cre mice from Jackson laboratory, Maine) (FIG. 5A). These PRR knockout mice (Nefh-PRR) appear to be vital and exhibit global PRR ablation in the brain regions that are involved in central regulation of BP, such as the subfornical organ (SFO) and paraventricular nucleus (PVN) (FIG. 5B), as well as the rostral ventral lateral medulla (RVLM), solitary nucleus (NTS), and non-CV regulatory nuclei.

Figure 6B:
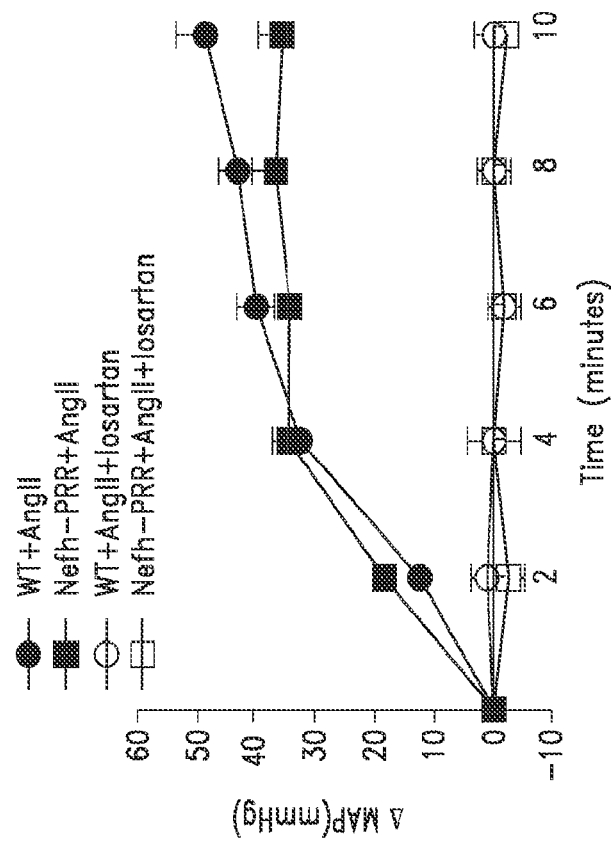
FIG. 6 is a series of graphs illustrating the pressor response to intracerebroventricular (ICV) infusion of carbachol (FIG. 6A), Ang II (FIG. 6B), renin (FIG. 6C), and prorenin (FIG. 6D) in wild-type (WT) and Nefh-PRR mice. WT and Nefh-PRR mice were implanted with telemetric transmitters and ICV cannula. Two weeks after recovery, mice were ICV infused (0.3μl/min) with carbachol (100 ng/μl), Ang II (100 ng/μl), Ang II (100 ng/μl)+losartan (10 μg/μl), mouse renin (100 ng/μl), mouse prorenin (100 ng/μl), or mouse prorenin (100 ng/μl)+losartan (10 μg/μl) over 10 minutes. Blood pressure (BP) was recorded in conscious freely moving mice. *$P<0.05$ vs. WT.
Figure 6A:
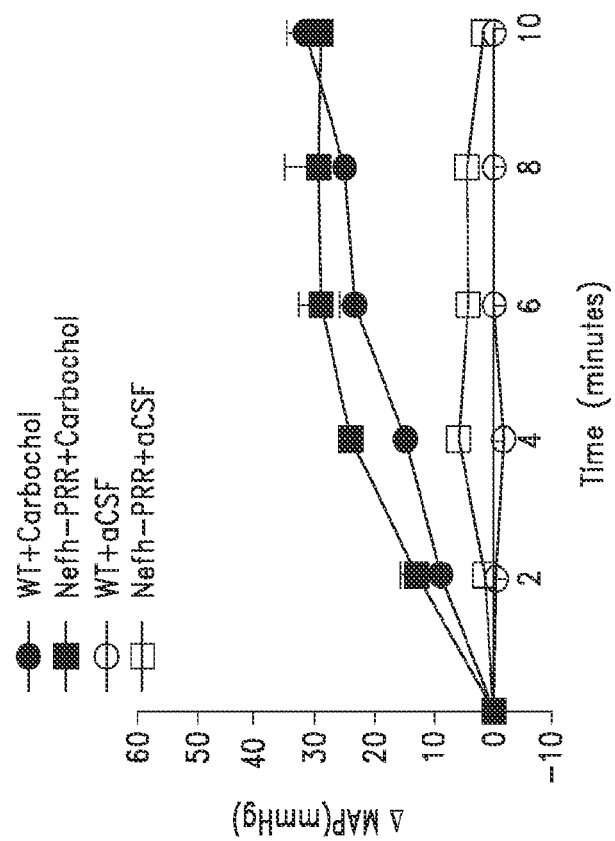
Figure 6D:
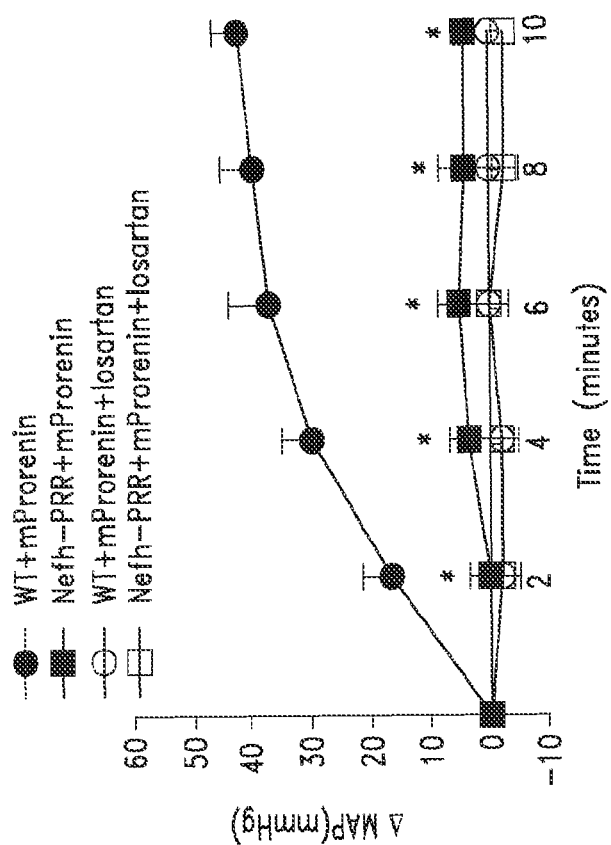
Figure 6C:
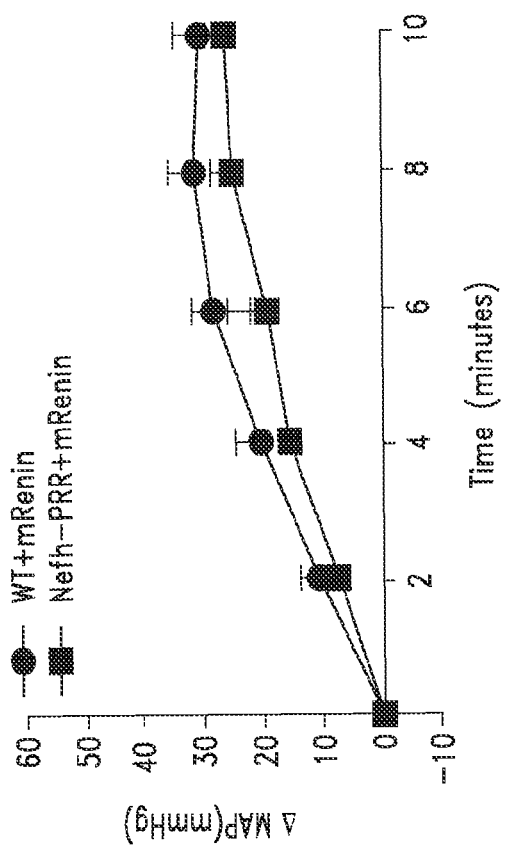

PRR is critical for early development. To test whether neurons are functionally intact in neuron-specific PRR knockout mice, carbachol (a cholinergic agonist), Ang II, renin, and prorenin were ICV infused to both Nefh-PRR and wild type (WT) mice. The pressor response to ICV infusion of carbachol and Ang II was similar between Nefh-PRR and wild type (WT) mice suggesting that the Nefh-PRR mice harbor functional acetylcholine receptor and AT1R (FIG. 6A, B). Interestingly, the pressor response to ICV prorenin was significantly reduced in Nefh-PRR compared to WT mice (FIG. 6D) indicating that the pressor response to prorenin requires PRR. In addition, the prorenin-induced pressor effect is primarily the direct action of prorenin but not from its conversion to renin, since the pressor response to ICV renin is similar between Nefh-PRR and WT mice (FIG. 6C). These data demonstrate that prorenin, via binding to PRR, regulates BP in the CNS.

Figure 7:
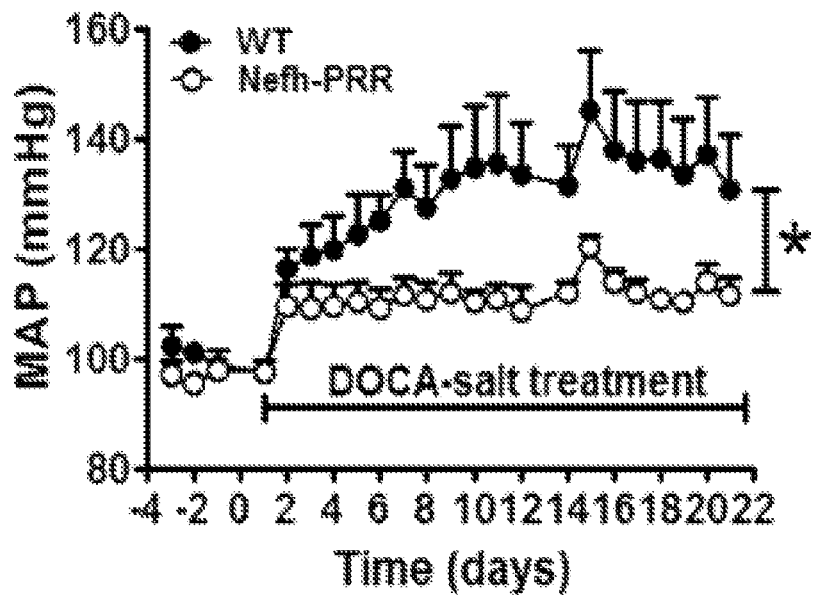
FIG. 7 is a graph illustrating reduced BP in Nefh-PRR mice in DOCA-salt hypertension. Mice were implanted with telemetry transmitters for BP recording and treated with DOCA-salt for 21 days.*$P<0.05$ VS. WT.

More importantly, although the baseline BP and HR were not different between Nefh-PRR and WT mice, the brain-targeted PRR deletion attenuated the development of DOCA-salt hypertension (FIG. 7), indicating a critical role of brain PRR in the development of hypertension. However, the mechanism by which PRR affects BP remains unclear.

Accordingly, without wishing to be bound by theory, it is hypothesized that brain-targeted PRR deletion reduces Ang II-dependent and Ang II-independent signaling pathways, leading to reduced sympathetic activity, improved baroreflex sensitivity, and ultimately reduced BP and improved CV function.

Telemetry BP recording, baroreflex and autonomic function analysis, and molecular biology techniques may be utilized to determine the role and mechanisms of PRR in the development of DOCA-salt hypertension. The control mice for Nefh-PRR mice experiments are wild type littermates (WT) that are heterozygous for Nefh-Cre to exclude the possible effects of Cre-mediated toxicity on phenotypes.

Example 3

Delineating the Autonomic Mechanisms and CV Consequences of Brain-Targeted PRR Deletion in the Development of DOCA-Salt Hypertension The Nefh-PRR and WT mice are implanted with telemetric transmitters and receive DOCA-salt, high salt only, or sham treatment as described above. Spontaneous baroreflex sensitivity (SBRS), cardiac, and vasomotor sympathetic tone are assessed as described previously (see, e.g., Li W, et al. Brain-targeted (pro)renin receptor knockdown attenuates angiotensin ii-dependent hypertension. *Hypertension*. 2012, 59:1188-1194; which is hereby incorporated by reference in its entirety). The SBRS is calculated at four different time points (0, 7, 14, and 21 days) without additional animals needed using the sequence method (Hemolab software). In addition, baroreflex reflex sensitivity (BRS) is assessed using a pharmacological method consisting of infusion of sodium nitroprusside (5 μg/min, iv) and phenylephrine (50 ng/min iv) to decrease and increase BP respectively after 21 days of DOCA-salt treatment. Autonomic function is assessed using intraperitoneal injection of propranolol (β-blocker, 4 mg/kg), methyl-atropine (muscarinic receptor blocker, 1 mg/kg), and chlorisondamine (ganglionic blocker, 5 mg/kg) as described previously.

Changes in HR or BP are calculated after administration of the antagonists. At the end of the protocol, echocardiography is performed as previously described, and mice are sacrificed after echocardiography. The hearts are collected for collagen deposition and cardiomyocyte diameter analysis to determine the degree of hypertrophy in the heart.

Plasma and urine are collected for norepinephrine (NE) measurement using a CatCombi ELISA kit (IBL International, Hamburg, Germany). PRR deletion will improve SBRS and reduce sympathetic activity due to reduced Ang II generation and its stimulation of AT1 receptors in the brain, and thus reverse cardiac hypertrophy and fibrosis following reduction of hypertension.

Example 4

Figure 8:
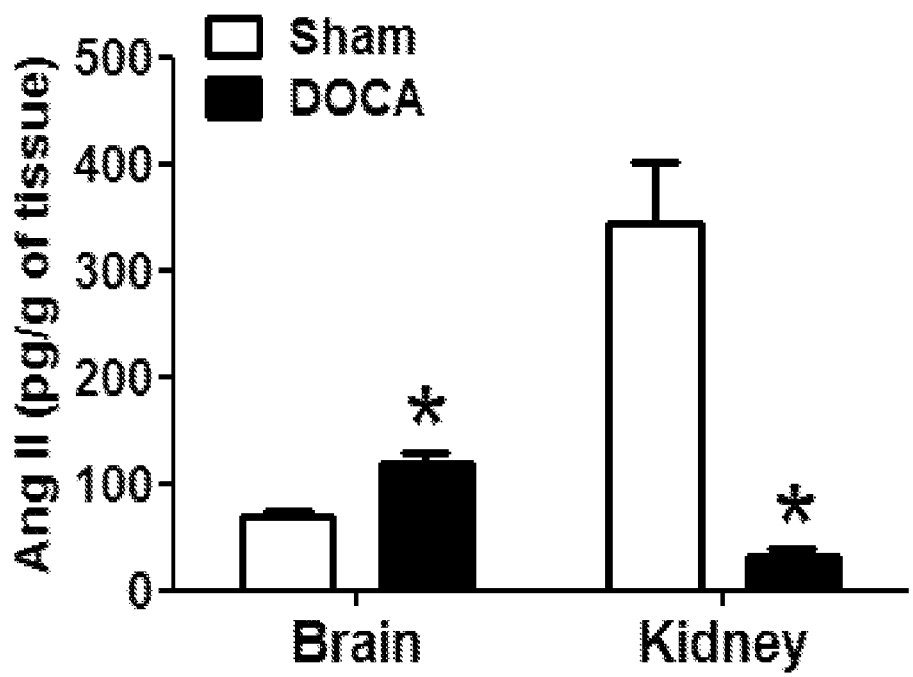
FIG. 8 is a graph illustrating Ang II levels in DOCA-salt hypertensive mice. Mice were treated with DOCA-salt or Sham for 21 days. Brain hypothalamus and kidney tissues were harvested for Ang II measurement using fluorescent ELISA KIT. *$P<0.05$ vs. WT.
Figure 9B:
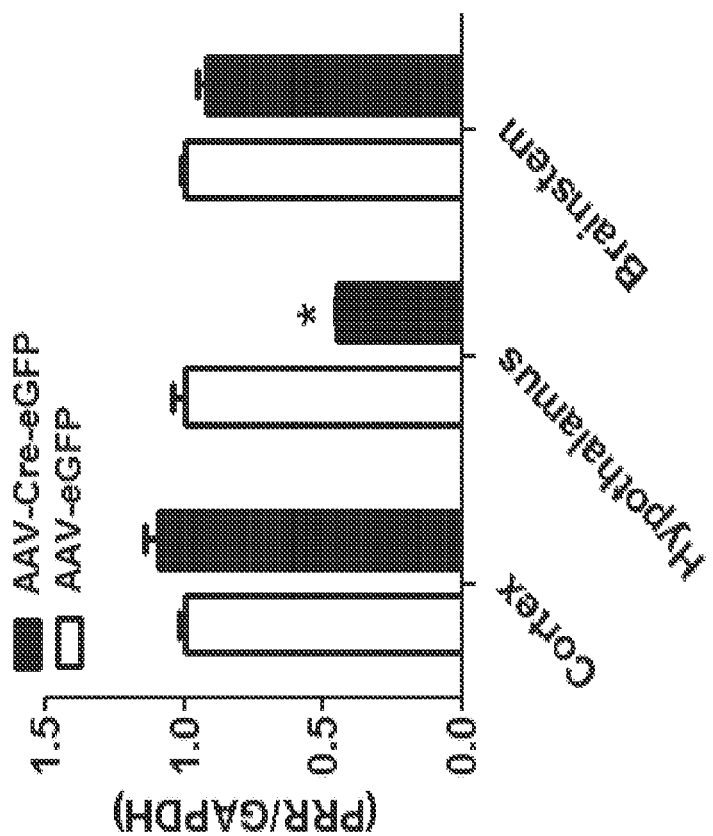
FIGS. 9A and 9B are graphs illustrating that ICV administration of AAV-Cre-eGFP reduces pressor response induced by ICV mouse prorenin in PRR-Floxed mice. The AAV-PRR-eGFP (100 nl) was administered ICV to PRR-Floxed mice. After 7 days, mice were ICV infused (0.3 μl/min) with mouse prorenin (100 ng/μl) over 10 minutes. BP was recorded in conscious freely moving mice (FIG. 9A). At the end of experiment, brain cortex, hypothalamus, and brainstem were harvested for PRR mRNA measurement (FIG. 9B). *$P<0.05$ vs. AAV-eGFP.
Figure 9A:
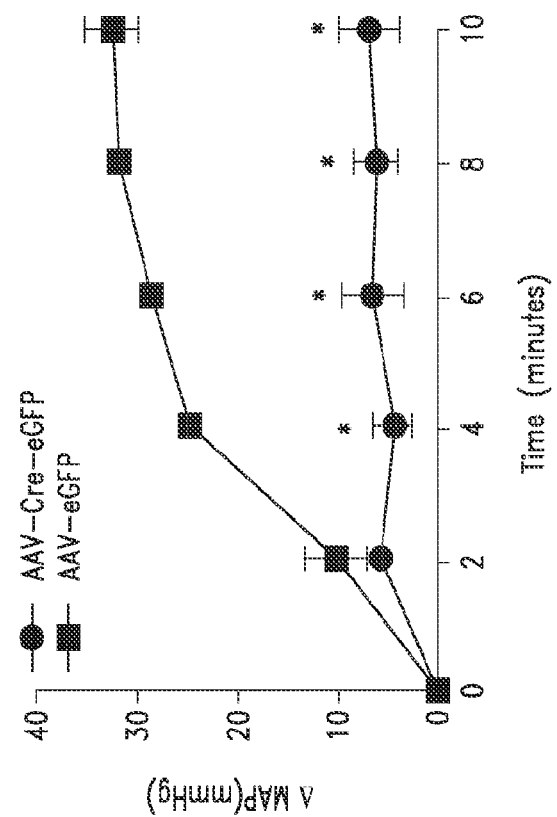

Determining the Effects of PRR Deletion on ACE/AngII/AT1R and ACE2/Ang1-7/MasR Axes in DOCA-Salt Hypertension The reduction of DOCA-salt hypertension by PRR deletion in the brain can result from a decrease of Ang II generation, thus leading to a lesser stimulation of AT1 receptors, or an inactivation of Ang II independent signals. Despite several reports showing PRR-mediated Ang II formation, the direct effects of brain PRR deletion on Ang II formation during hypertension remained unknown. An Ang II measurement assay has been established, and using the assay, an increase in brain Ang II level was found despite a decrease in kidney Ang II level in the DOCA-salt hypertensive mice (FIG. 8).

The Nefh-PRR and WT mice receive DOCA-salt, high salt, or sham treatment as described above. At the end of 21 days of treatment, mice are sacrificed; plasma and brain tissues are harvested for Ang II, Ang 1-7 measurement utilizing an ELISA kit (Phoenix Pharmaceutical Inc.). FIG. 8 shows the ability to measure the Ang II levels in WT mice receiving either DOCA-salt or sham treatment. ACE, ACE2, AT1R, and MasR mRNA and protein levels may be determined using real time PCR, immunofluorescent staining, and western blotting as described. The radioligand receptor binding assay for AT1R is performed to determine the levels of functional receptors as described. The ACE and ACE2 activity are measured to evaluate the function of the enzymes using Fluorogenic Peptide VI.

Data is expressed as mean±SEM. Data is analyzed by one-way or two-way, repeated measures ANOVA followed by Student's modified t-test with Bonferroni correction for multiple comparisons between means using the modified error mean square term from the ANOVA.

Example 5

PRR Antagonist Peptides Blocked the Prorenin-Induced Increase in BP

C57Bl/6J mice (N=5/group) were each implanted with a telemetric probe for BP recording and an intracerebroventricular (ICV) cannula for infusion of mouse prorenin (100 ng/ul), PR10, or PR20 (45 ng/ul) at 0.3 ul/minute for 10 minutes. Mouse prorenin infusion increased the BP (mmHg) in WT mice (ΔMAP: 31.3±1.1); however, the prorenin-induced pressor response was abolished in either PR10 (ΔMAP: 16.9±4.4 vs. prorenin) or PR20 (ΔMAP: 12.7±0.5 vs. prorenin) infused mice. Both of the peptides exhibited a 40-50% reduction in pressor response induced by prorenin.

Example 6

Exemplary Method for Constructing Plasmids for Thioether Bridge-Modified Peptides To avoid peptide degradation by peptidase in vivo, thioether-bridge modified peptides were designed according to the core amino acid sequence of PR10 and PR20. The NisBTC-encoding plasmid (pTU-BTC) and substrate-peptide-encoding plasmids (pPR103, pPR105, pPR107, pPR201, pPR202) are constructed and introduced into the lactic acid producing bacterium *Lactococcus lactis* to produce the thioether-bridged peptides PR103, PR105, PR107, PR201 and PR202 respectively.

Figure 10:
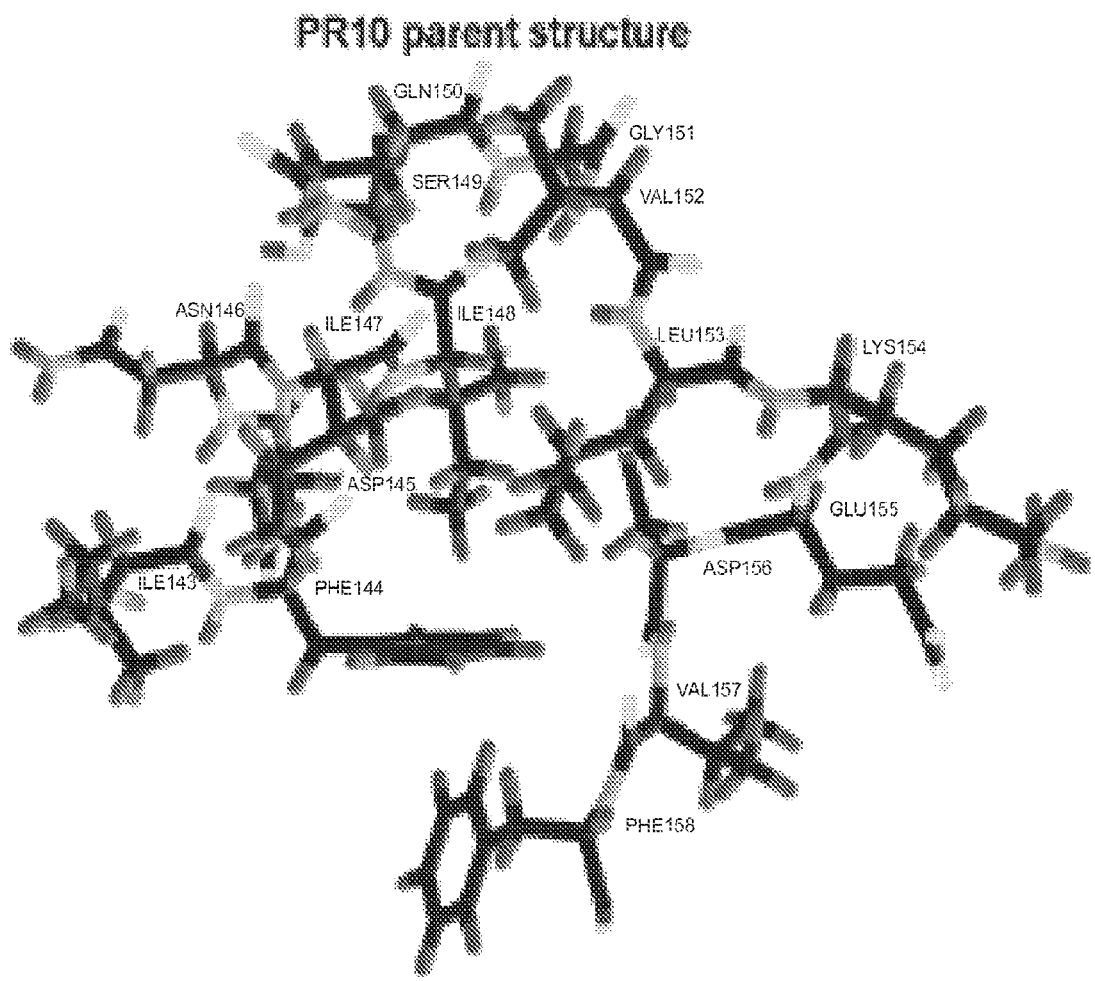
FIG. 10 is a diagram illustrating the 3D structure of PR10 (SEQ ID NO:1).
Figure 11:
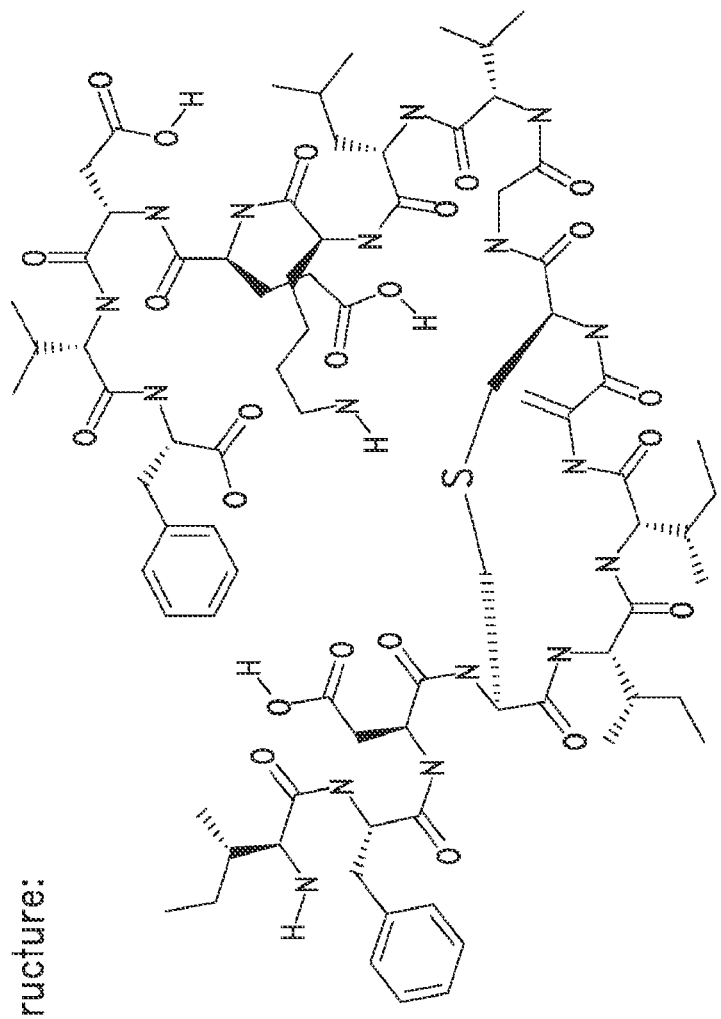
FIG. 11 shows the amino acid sequence and chemical structure of modified peptide PR103 (SEQ ID NO:3) with a thioether bridge and one non-standard amino acid, dehydroalanine (Dha), at position 7. dehydroalanine (Dha), 2-aminobutyric acid (Abu), and dehydrobutyrine
Figure 12:
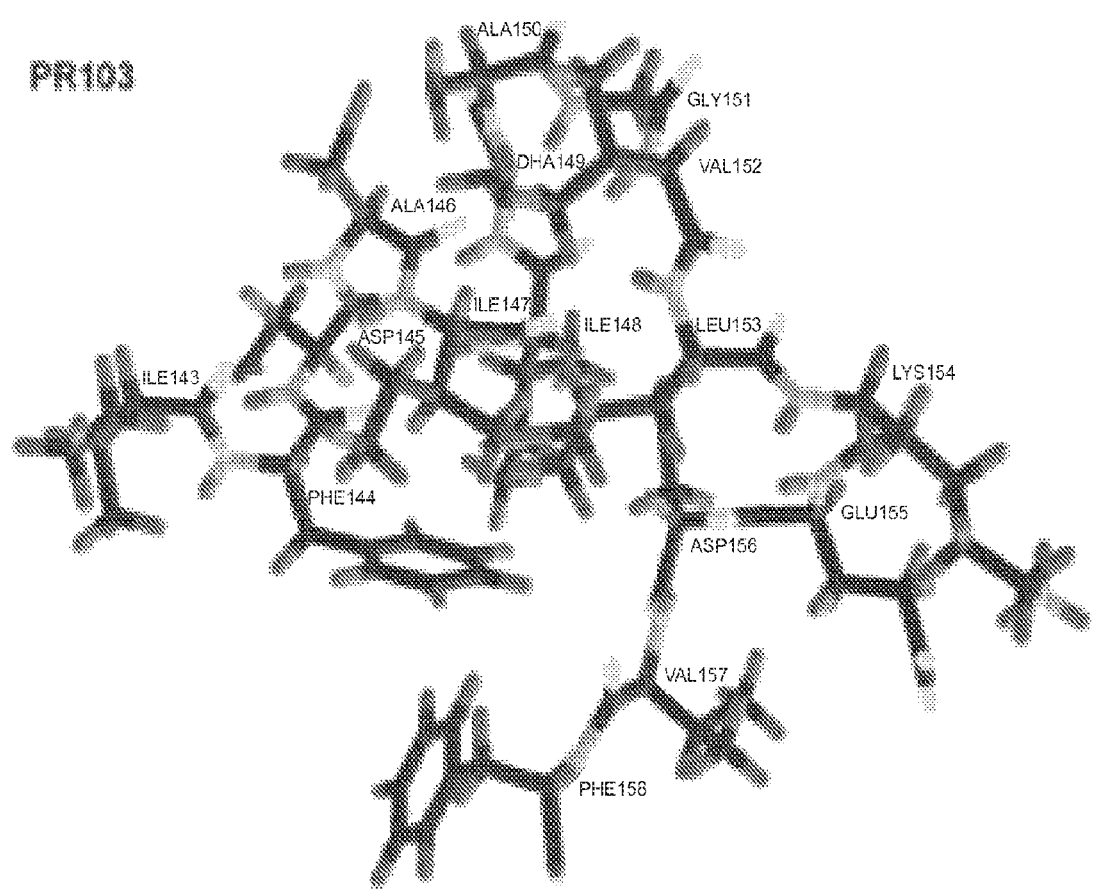
FIG. 12 is a diagram illustrating the 3D structure of modified peptide PR103.
Figure 13:
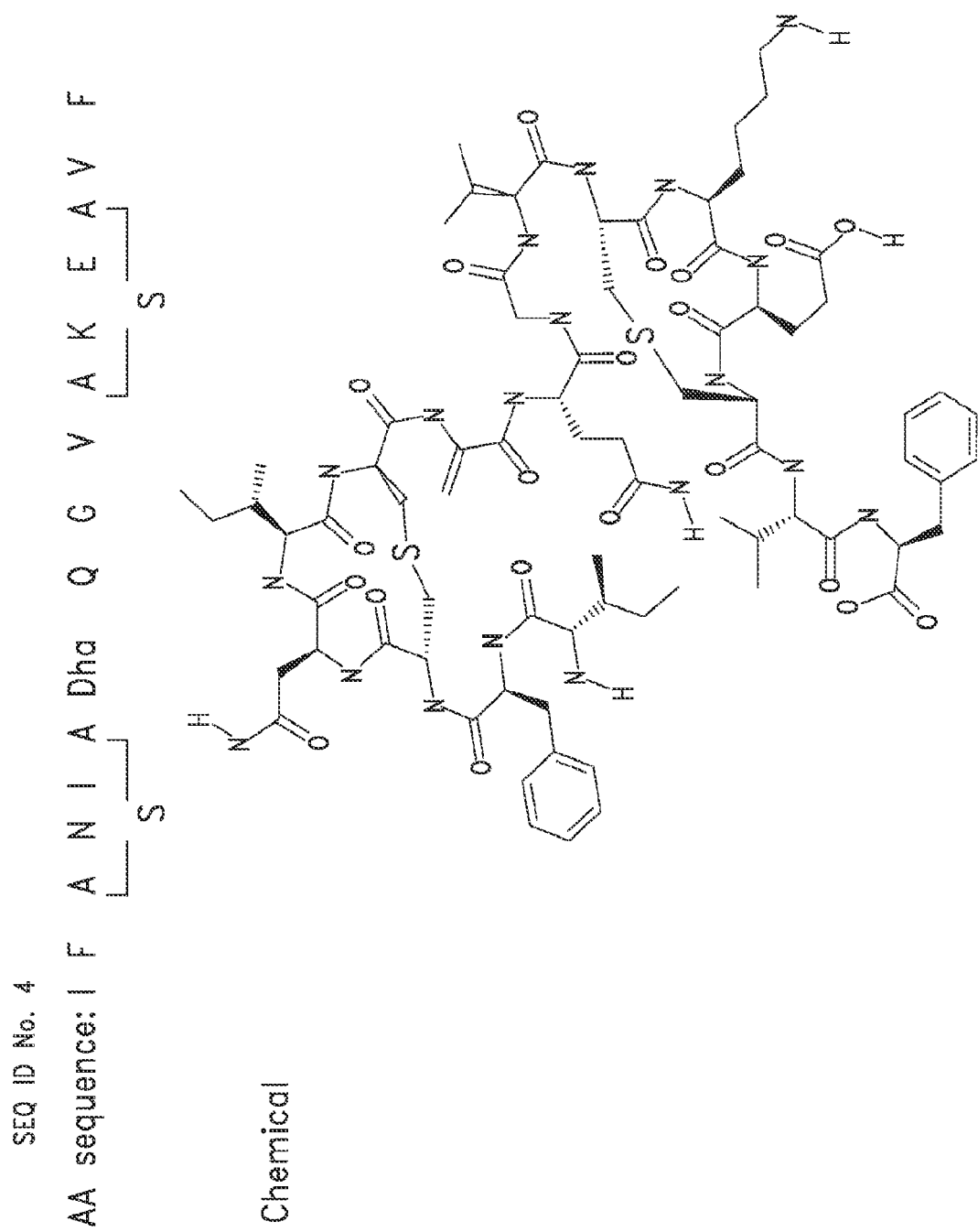
FIG. 13 shows the amino acid sequence and chemical structure of modified peptide PR105 (SEQ ID NO:4) with two thioether bridges and one non-standard amino acid, dehydroalanine (Dha), at position 7.
Figure 14:
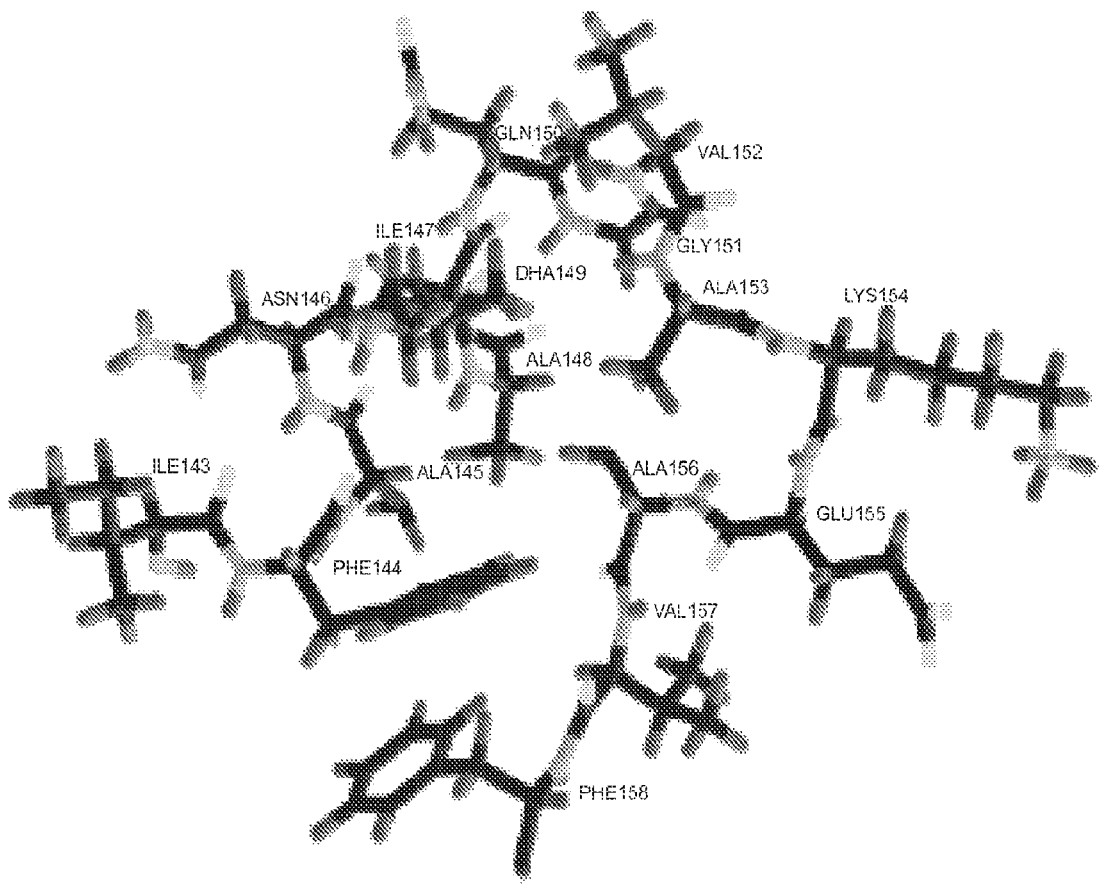
FIG. 14 is a diagram illustrating the 3D structure of modified peptide PR105.
Figure 15:
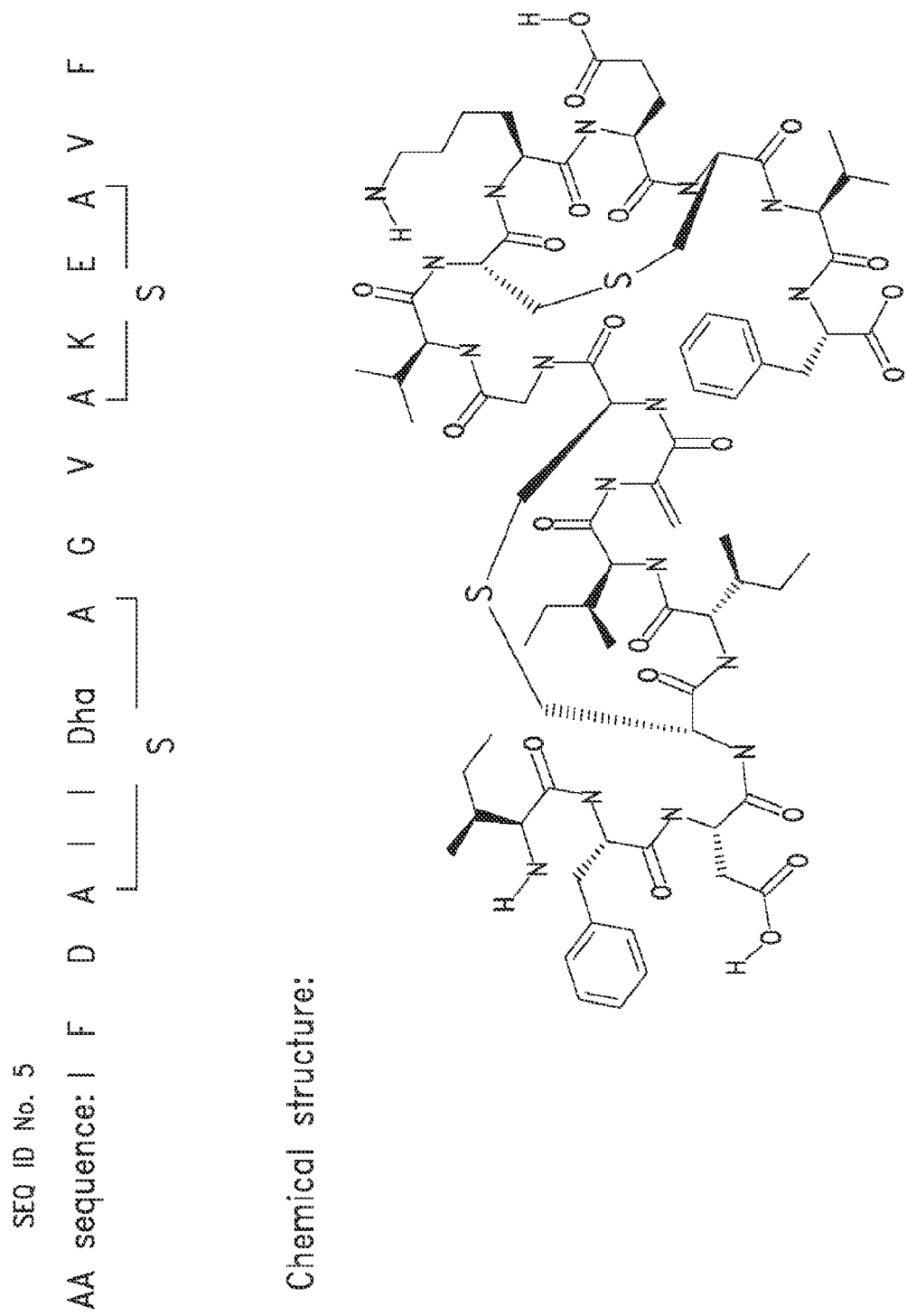
FIG. 15 shows the amino acid sequence and chemical structure of modified peptide PR107 (SEQ ID NO:5) with two thioether bridges and one non-standard amino acid, dehydroalanine (Dha), at position 7.
Figure 16:
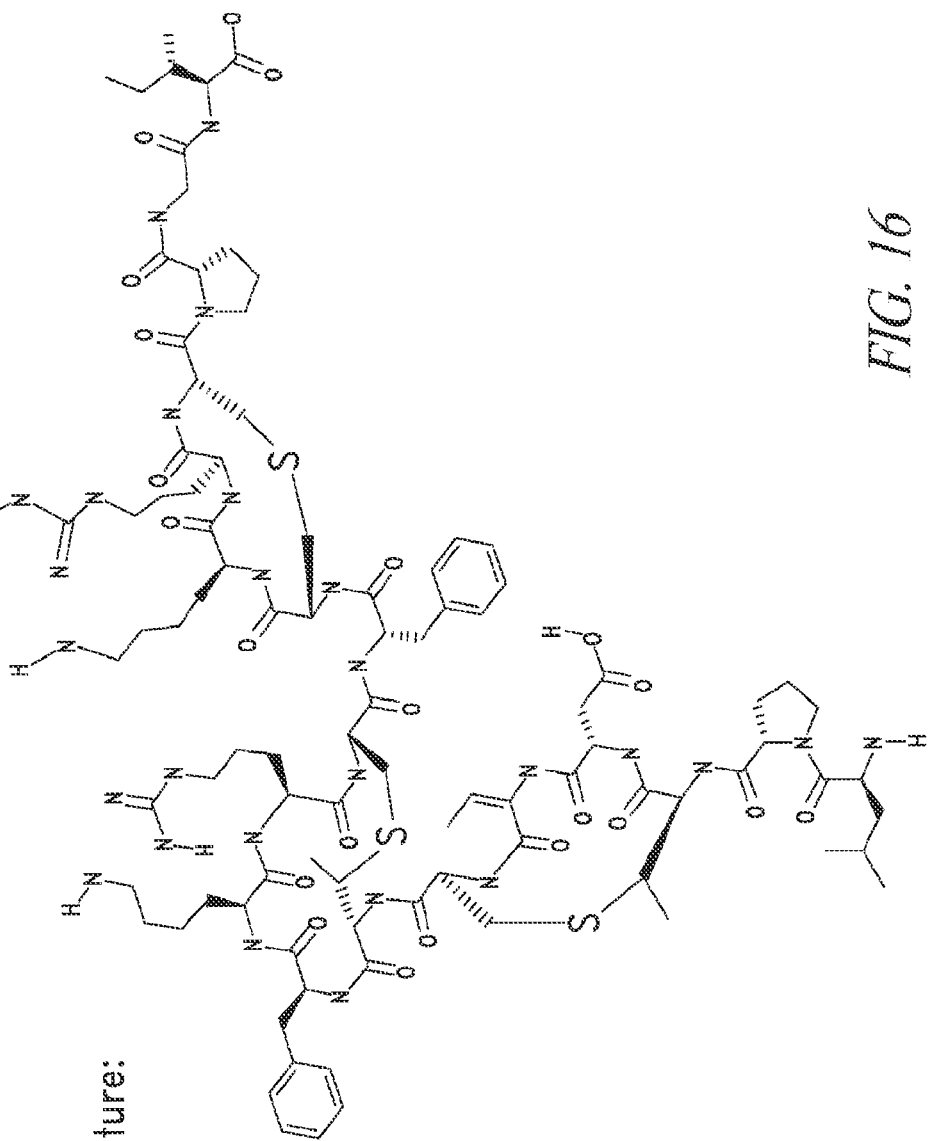
FIG. 16 shows the amino acid sequence and chemical structure of modified peptide PR201 (SEQ ID NO:6) with three thioether bridges and four non-standard amino acids, 2-aminobutyric acid (Abu, at positions 3 and 7), dehydrobutyrine (Dhb, at position 5), and dehydroalanine (Dha, at position 18).
Figure 17:
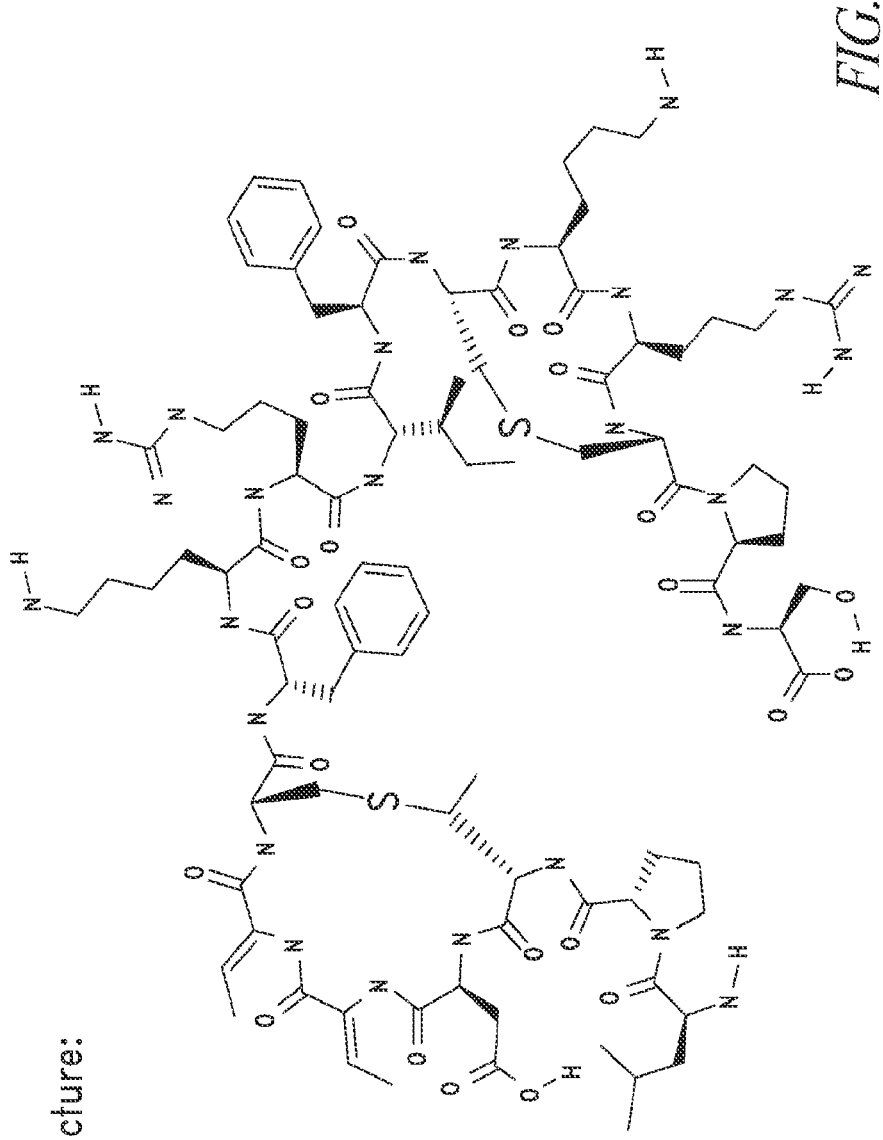
FIG. 17 shows the amino acid sequence and chemical structure of modified peptide PR202 (SEQ ID NO:7) with two thioether bridges and four non-standard amino acids, 2-aminobutyric acid (Abu, at position 3), dehydrobutyrine (Dhb, at positions 5 and 6), and dehydroalanine (Dha, at position 18).

Computational modeling was used to design modified PR10 and PR20 peptides comprising thioether-bridges. The thioether-bridges were designed according to the three-dimensional (3D) structure of human renin (provided on the NCBI's website at the following address: ncbi.nlm.nih.gov/Structure/mmdb/mmdbsrv.cgi?uid=65019). Computational modeling was used to confirm the similarity of the thioether-bridge modified peptides to the original human renin peptide. Examples of the computational 3D structures are shown in FIGS. 10, 12, and 14.

Example 7

Design and Construction of the Ptu-Btc Expression Vector

The genomic DNA from strain NCTC 6681 *Lactococcus lactis* subsp.*lactis*, which contains the nisBTC gene, purchased from American Type Culture Collection (ATCC), was used to prepare the vector. Primers for fusion nisBTC gene PCR were designed: Pnis forward: 5'-ttgagtcttaaacat-acttgaatgacc-3' (SEQ ID NO:9), reverse: 5'-gaacttttatcatttt-gagt gcctccttata-3' (SEQ ID NO:10); PnisBTC forward: 5'-ggcactcaaaatgataaaaagttcatttaaagctc-3' (SEQ ID NO:11), reverse: 5'-cttctcatttcctcttccctcc-3' (SEQ ID NO:12). Pfusion forward: 5'-ctagtcttataactatactgacaatag-3' (SEQ ID NO:13), reverse: 5'-tcatttcctcttccctccttc-3' (SEQ ID NO:14). The PCR product will be inserted into NICE pNZ9530 *Lactococcus lactis* nisRnisK vector and amplified in NZ9000 *L. Lactis* (purchased from Boca Scientific).

Example 8

Design and Construction of Prr Antagonist Peptides

The NisA leader peptide (MSTKDFNLDLHHHHHHDS-GASPRITSISLCTPGCK TGALM, SEQ ID NO:15) was designed, which comprises of a His tag for purification and a thrombin cleavage site for generating target peptide without extra amino acid residues. The polynucleotide sequences coding for peptides PR10 and PR20 were optimized to *L. lactis* for higher expression efficiency using Optimizer software (available at the following web address: genomes.urv.es/OPTIMIZER/). The DNA sequences coding for peptides were synthesized with ScaI and XbaI restriction enzyme sites for cloning into the NICE pNZ8150 expression vector to form pPR103, pPR105, pPR107, pPR201, and pPR202 constructs. Expression of PRR antagonist peptides was achieved by co-transfection of pTU-BTC with pPR103, pPR105, pPR107, pPR201, or pPR202 in the NZ9000 *L. Lactis*.

Example 9

Purification of PRR Antagonist Peptides

The PRR antagonist peptides are expressed in the cell culture medium. Peptides with a 6×His tag are purified through Nichel nitrilotriacetic (Ni-NTA) resin. The purified thioether-bridge containing peptides are tested for antagonist activity to PRR in animal models of hypertension and other diseases.

Example 10

Identification of Amino Acid Residues Involved in PRR Binding

In order to determine which residues of the PR20 antagonist peptide are involved in binding PRR, an alanine replacement assay was performed. A series of peptides comprising a single alanine substitution at each of the 19 amino acid positions were generated. Each of the 19 alanine substituted peptides and the PR20 peptide were labeled with FITC. Using fluorescent microscopy, each peptide was examined for binding to PRR in mouse brain sections.

Figure 20:
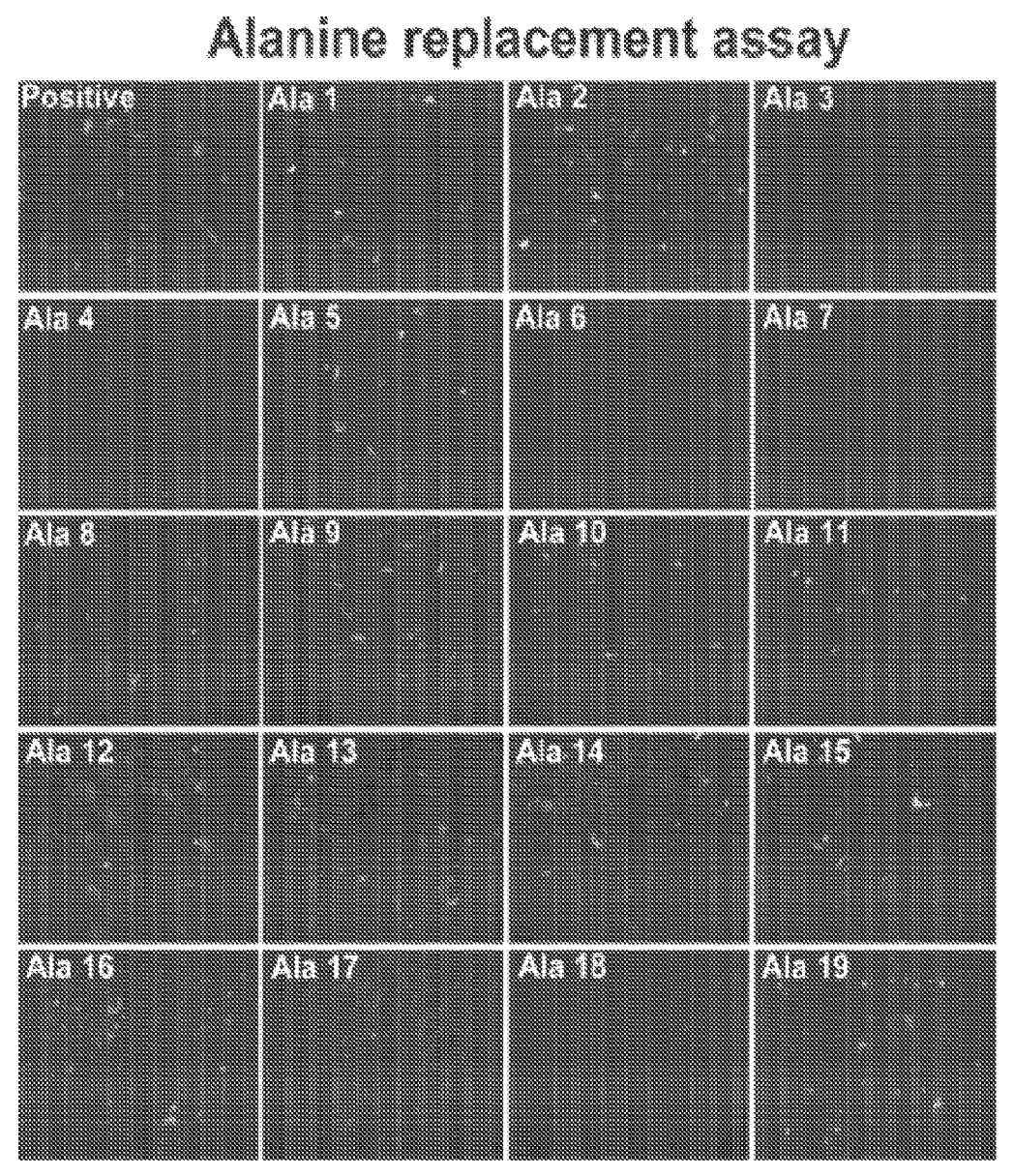

As shown in FIG. 20, the amino acids at positions 3, 4, 6, 7, 18 are essential for PR20 binding to PRR. Amino acids at positions 8, 10, 11 were identified as being important, but not critical, for PR20 binding to PRR.

Example 11

PRR Antagonist Peptides PR30 and PR40

Two additional PRR antagonist peptides, PR30 (SEQ ID NO:16) and PR40 (SEQ ID NO:17), were derived from the core amino acid sequence of PR20. Amino acid residues 3, 4, 6, 7, and 18 (FIGS. 21 and 22; underlined, bold text) of PR30 and PR40 correspond to the positions that are essential for binding to PRR. Amino acid residues 8, 10, 11, and 14 were determined to be involved in PRR binding, but not essential (FIGS. 21 and 22, bold, italicized text). The polynucleotides encoding the peptides were codon optimized for expression in *L. lactis* using Optimizer software, and computational modeling was used to design modified PR30 and PR40 peptides comprising thioether-bridges.

As described above, the thioether-bridges were designed according to the three-dimensional (3D) structure of human renin. Computational modeling was used to confirm the similarity of the thioether-bridge modified peptides to the original human renin peptide. As shown in FIG. 21, two modified peptides derived from PR30 comprising a single thioether bridge were designed, PR301 (SEQ ID NO:18) and PR302 (SEQ ID NO:19), and one modified peptide was designed with two thioether bridges, PR303 (SEQ ID NO:20). Similarly, two modified peptides comprising a single thioether bridge were derived from PR40, PR401 (SEQ ID NO:21) and PR402 (SEQ ID NO:22), and one modified peptide with two thioether bridges was also designed, PR 403 (SEQ ID NO:23), as shown in FIG. 22.

While certain novel features of this invention shown and described below are pointed out in the claims, the invention is not intended to be limited to the details specified, since a person of ordinary skill in the relevant art will understand that various omissions, modifications, substitutions and changes in the forms and details of the invention illustrated and in its operation may be made without departing in any way from the spirit of the present invention. No feature of the invention is critical or essential unless it is expressly stated as being "critical" or "essential."

All patents, patent applications, and references cited herein are incorporated in their entireties by reference.

REFERENCES CITED

Nguyen G, et al. *J Clin Invest.* 2002; 109:1417-1427
Shan Z, et al. *Exp Physiol.* 2008; 93:701-708
Kaneshiro et al. *J Am Soc Nephrol.* 2007; 18:1789-1795
Hirose T, et al. *Am J Hypertens.* 2009; 22:294-299
Ott C, et al. *Pharmacogenet.* 2011; 21:347-349.
Zubcevic J, et al. *Hypertension.* 2011; 57:1026-1033
Primatesta P, et al. 1998. *Hypertension.* 2001; 38:827-832
Fisher J P, Fadel P J. *Exp Physiol.* 2010; 95:572-580
Paul M, et al. *Arzneimittel-Forschung.* 1993; 43:207-213
Davisson R L. *Am J Physiol—Regul Integr Comp Physiol.* 2003; 285:R498-R511 Davisson R L, Sigmund C D. Pediatr Nephrol. 1996; 10:798-803
Denser AHJ, Deinum J. *Hypertension.* 2005; 46:1069-1076
Denser AHJ. *Hypertens Res.* 2009; 33:4-10
Paul M, et al. *Physiol Rev.* 2006; 86:747-803
Paton J F, Raizada M K. *Exp Physiol.* 2010; 95:569-571
Ferrario C M. *Hypertension.* 2006; 47:515-521
Ferreira A J, et al. *Am. J. Respir. Crit. Care Med.* 2009; 179:1048-1054
Xu P, et al. *Am J Physiol Regul Integr Comp Physiol.* 2010; 300:R804-R817 Cuadra A E, et al. *Pharmacology & Therapeutics.* 2010; 125:27-38
Bader M, Ganten D. *Circ Res.* 2002; 90:8-10
Lippoldt A, et al. *J Mol Med.* 2001; 79:71-73
Kinouchi K, et al. *Circ Res.* 2010; 107:30-34
Burckle C, Bader M. *Hypertension.* 2006; 48:549-551
Krebs C, et al. *Kidney Int.* 2007; 72:725-730
Shan Z, et al. *Circ Res.* 2010; 107:934-938
Connelly K A, et al. *Journal of Hypertension.* 2011; 29:1175-1184 1110.1097/HJH.1170b1013e3283462674
Siragy H M, Huang J. *Experimental Physiology.* 2008; 93:709-714
Blaustein M P, et al. *American Journal of Physiology-Heart and Circulatory Physiology.* 2012; 302:H1031-H1049
Nishimura M, et al. *The American journal of physiology.* 1998; 274:R635-644
Janiak P C, et al. *American Journal of Physiology—Regulatory, Integrative and Comparative Physiology.* 1990; 259:R1025-R1034
Yemane H, et al. *Exp Physiol.* 2009; 95:51-55
Xu H, et al. *American Journal of Physiology-Heart and Circulatory Physiology.* 2007; 293:H160-H168
Grobe J L, et al. *Hypertension.* 2011; 57:600-607
Chen Q H, Toney G M. *American Journal of Physiology—Regulatory, Integrative and Comparative Physiology.* 2001; 281:R1844-R1853
Shi P, et al. *American Journal of Physiology-Regulatory, Integrative and Comparative Physiology.* 2007; 293: R2279-R2289
Toney G M, Stocker S D. The *Journal of Physiology.* 2010; 588:3375-3384
Feng Y, et al. *Circ Res.* 2010; 106:373-382
Osborn J W, et al. *Curr Hypertens Rep.* 2007; 9:228-235
Ito K, et al. *Circ Res.* 2009; 104:1004-1011
Zimmerman M C, et al. *Circ Res.* 2004; 95:210-216
Hou X, et al. *American Journal of Physiology—Regulatory, Integrative and Comparative Physiology.* 2009; 296: R1427-R1438
Eide L M, C. T. *Biotechniques.* 2005; 38:99-104
Brewer G J, Torricelli J R. *Nat. Protocols.* 2007; 2:1490-1498
Huang B S, et al. *American Journal of Physiology-Heart and Circulatory Physiology.* 2004; 287:H1160-H1166
Nguyen G. *Curr Opin Nephrol Hypertens.* 2007; 16:129-133
Satofuka S, I et al. *Am J Pathol.* 2008; 173:1911-1918
Merrill D C, et al. *J Clin Invest.* 1996; 97:1047-1055
Thompson M W, et al. *Hypertension.* 1996; 28:290-296
Chen X, et al. *Am J Physiol.* 1997; 272:F299-F304
Lazartigues E, et al. *Circ Res.* 2002; 90:617-624
Makrides S C, et al. *Hypertension.* 1988; 12:405-410
Schenk J, McNeill J H. *J Pharmacol Toxicol Methods.* 1992; 27:161-170
Gutkind J S, et al. *Am J Physiol.* 1988; 255:H646-H650
Nguyen G, Denser AHJ. *Expert Opin Investig Drugs.* 2006; 15:1131-1135
Nguyen G, Contrepas A. *Curr Opin Pharmacol.* 2008; 8:127-132
Oshima Y, et al. *J Am Soc Nephrol.* 2011; 22:2203-2212
Riediger F, et al. *J Am Soc Nephrol.* 2011; 22:2193-2202
Hans C P, et al. *PLoS ONE.* 2009; 4:e7430
Lazartigues E, et al. *Fundam Clin Pharmacol.* 1998; 12:643-645
Feng Y, et al. *FASEB J.* 2009; 23:802.801
Hans C P, et al. *Cardiovasc Pathol.* 2010; 20:e57-68
Ichihara A, et al. *J. Clin. Invest.* 2004; 114:1128-1135
Batenburg W W, et al. *J Hypertens.* 2007; 25:2441-2453

Ferrario C M. *Curr Opin Nephrol Hypertens.* 2011; 20:1-6
Raizada M K, Ferreira A J. *J Cardiovasc Pharmacol.* 2007; 50:112-119
Feng Y, et al. *Circ Res.* 2008; 102:729-736
Xia H, et al. *FASEB J.* 2008; 22:1236
Takahashi K, et al. *J Neuroendocrinol.* 2010; 22:453-459
Radin M J, et al. *Clin Exp Hypertens.* 2008; 30:541-552
Lal A, et al. *Am J Hypertens.* 2003; 16:319-323
Muller D N, et al. *Annals of medicine.* 2012; 44 Suppl 1:S43-48
Feldt S, et al. *Hypertension.* 2008; 51:682-688
Cruciat C M, et al. *Science.* 2010; 327:459-463
Crider B P, Xie X-S. *J Biol Chem.* 2003; 278:44281-44288
Moriyama Y, et al. *J Exp Biol.* 1992; 172:171-178
Allen A M. *Hypertension.* 2002; 39:275-280
Wei S G, et al. *J Hypertens.* 2009; 27:543-550
Freeman K L, Brooks V L. *Am J Physiol Regul Integr Comp Physiol.* 2007; 292:R1675-1682
Nakata T, et al. *Am J Hypertens.* 1989; 2:625-630
Berecek K H, *Hypertension.* 1982; 4:131-137
Nguyen G, Muller D N. *J Am Soc Nephrol.* 2010; 21:18-23
Biswas K B, *Front Biosci* (Elite Ed). 2010; 2:1234-1240
de Vries, L., et al. (2010) *Peptides* 31, 893-898
Kuipers, A., et al. (2009) *Appl. Environ. Microbiol.* 75, 3800-3802.
A. Ichihara, et al. *J. Clin. Invest.,* 114 (2004), pp. 1128-1135
Nabi A H, et al. Biochim Biophys Acta. 2009 December; 1794(12):1838-47. Epub 2009 September 3.
Li W, et al. *Hypertension.* 2012; 59:1188-1194

What is claimed is:

1. A method for treating hypertension comprising administering an effective amount of one or more (pro)renin receptor (PRR) antagonists to a patient in need thereof, wherein at least one of the one or more PRR antagonists is a polypeptide comprising the sequence of SEQ ID NO:17, and wherein the polypeptide comprises 30 amino acids or less.

2. A method for reducing blood pressure comprising administering a PRR antagonist to a patient in need thereof, wherein the PRR antagonist is a polypeptide comprising the sequence of SEQ ID NO:17, or the sequence of SEQ ID NO:17 with a non-standard amino acid at one or more of positions 3, 5, and 7, and wherein the polypeptide comprises 30 amino acids or less.

3. The method of claim 2, wherein the PRR antagonist is a PRR-binding peptide.

4. The method of claim 2, wherein the non-standard amino acid is dehydroalanine, 2-aminobutyric acid or dehydrobutyrine.

5. The method of claim 3, wherein the PRR antagonist comprises a thioether bridge.

6. The method of claim 2, wherein the administering step is oral, intravenous, or intracerebroventricular.

7. The method of claim 2, wherein the PRR antagonist reduces Ang II generation and prevents Ang II-independent signal activation.

* * * * *